(12) United States Patent
Winqvist et al.

(10) Patent No.: US 8,211,424 B2
(45) Date of Patent: *Jul. 3, 2012

(54) METHOD FOR TREATING MALIGNANT MELANOMA

(75) Inventors: Ola Winqvist, Uppsala (SE); Magnus Thörn, Uppsala (SE)

(73) Assignee: SentoClone International AB, Stockholm (SE)

(*) Notice: Subject to any disclaimer, the term of this patent is extended or adjusted under 35 U.S.C. 154(b) by 880 days.

This patent is subject to a terminal disclaimer.

(21) Appl. No.: 12/158,681

(22) PCT Filed: Dec. 20, 2006

(86) PCT No.: PCT/EP2006/012306
§ 371 (c)(1),
(2), (4) Date: Oct. 22, 2008

(87) PCT Pub. No.: WO2007/071390
PCT Pub. Date: Jun. 28, 2007

(65) Prior Publication Data
US 2009/0220472 A1    Sep. 3, 2009

(30) Foreign Application Priority Data
Dec. 21, 2005 (DK) .................................. 2005 01809

(51) Int. Cl.
*A01N 63/02* (2006.01)
*A61K 35/02* (2006.01)
*A61K 35/26* (2006.01)

(52) U.S. Cl. ................... 424/93.71; 424/534; 424/578

(58) Field of Classification Search ........................ None
See application file for complete search history.

(56) References Cited

U.S. PATENT DOCUMENTS

| | | | |
|---|---|---|---|
| 4,478,815 A | 10/1984 | Burchiel et al. | |
| 5,767,065 A | 6/1998 | Mosley et al. | |
| 5,814,295 A | 9/1998 | Martin et al. | |
| 7,012,098 B2 | 3/2006 | Manning et al. | |
| 7,951,365 B2* | 5/2011 | Winqvist et al. | 424/93.71 |
| 2002/0182730 A1 | 12/2002 | Gruenberg | |
| 2003/0129749 A1 | 7/2003 | Gundersen et al. | |
| 2003/0228635 A1 | 12/2003 | Hu et al. | |
| 2006/0104950 A1 | 5/2006 | Okano et al. | |
| 2007/0141026 A1 | 6/2007 | Winqvist et al. | |
| 2009/0022695 A1 | 1/2009 | Winqvist et al. | |
| 2009/0074714 A1 | 3/2009 | Winqvist et al. | |
| 2009/0081175 A1* | 3/2009 | Winqvist et al. | 424/93.71 |
| 2009/0123443 A1 | 5/2009 | Winqvist et al. | |
| 2009/0297489 A1 | 12/2009 | Winqvist et al. | |
| 2010/0015161 A1 | 1/2010 | Winqvist et al. | |

FOREIGN PATENT DOCUMENTS

| | | |
|---|---|---|
| EP | 645147 A1 | 3/1995 |
| EP | 1408106 | 4/2004 |
| JP | 7-179352 A | 7/1995 |
| JP | 2002-519019 A | 7/2002 |
| WO | 97/46256 A | 12/1997 |
| WO | WO 99/53949 | 10/1999 |
| WO | 00/00587 A1 | 1/2000 |
| WO | 01/05433 A1 | 1/2001 |
| WO | 2004/012681 A1 | 2/2004 |
| WO | WO 2004016154 | 2/2004 |
| WO | 2004/032951 A1 | 4/2004 |
| WO | WO 2004/045650 | 6/2004 |

OTHER PUBLICATIONS

Farzad et al, Melanoma Research, 7(2):S59-S65 (1997).
Meijer et al, Proceedings of the American Association for Cancer Research, 42:683-684 (2001), Abstract.
Wedgewood Pharmacy (http://www.wedgewoodpharmacy.com/isosulfan/2004).
Meijer et al, J. Clin. Pharmacol, 441:81S-94S (Jul. 2001).
Santin et al, Am J. Obstet Gynecol., 183:601-609 (2000).
Kan et al, Biotherapy, 6:245-250 (1994).
Stratagene Catalog, p. 39 (1983).
Elliot et al, Current Opinion in Immunology, 13:625-633 (2001).
Martis et al, British Journal of Cancer, 94(10):1478-1484 (2006).
Tanis, Breast Cancer Research, 3:109-112 (2001).
Janeway et al, Immunobiology 5, Garland Science, 2001, Fig. A24.
Janeway et al, Immunobiology 5, Garland Science, 2001, Appendix III.
Harada et al, Immunology, 87:447-453 (1996).
Spits et al, J. Immunology, 139:1142-1147 (1987).
Hofman et al, J. Immunology, 141:1186-1190 (1988).
Perussia et al, J. Immunology, 149:3495-3502 (1992).
Biron, Immunity, 14:661-664 (2001).
Byers, CA Cancer J Clin, 49(6):353-361 (1999).
Okamoto et al, Cancer Immunol and Immunotherap, 40:173-181 (1995).
Dudley et al, Nature Reviews Cancer, 3:666-675 (2003).
Lind et al, Surgical Oncology, 2:273-282 (1993).
Bowie et al, Science, 257:1306-1310 (1990).
Cochran et al, Mod. Pathol., 14(6):604-608 (2001).
Frisell et al, Eur. J. Surg., 167:179-183 (2001).
Leong et al, Annals of Surgical Oncology, 9(1):82-87 (2002).
Yamshchikov et al, Int. J. Cancer, 92:703-711 (2001).
Kaiser, Science, 31:1370 (2006).
Mesel-Lemoine et al, Blood, 107(1):381-388 (2006).
Zhou et al, Blood, 107(2):628-636 (2006).
Sakaguchi, Nature Immunology, 6(4):345-352 (Apr. 2005).
Moore, Clinically Oriented Anatomy, Baltimore: Williams & Wilkins, 1985, pp. 41-46.

(Continued)

*Primary Examiner* — Michail Belyavskyi
(74) *Attorney, Agent, or Firm* — Porter Wright Morris & Arthur

(57) ABSTRACT

The present invention discloses an immunotherapeutic method for treating patients suffering from malignant melanoma, by administering expanded tumour-reactive CD4+ helper and/or CD8+ T-lymphocytes obtainable from one or more sentinel or metinel lymph nodes draining a malignant melanoma or a metastasis arising from malignant melanoma. The present invention provides a new effective method for treating malignant melanoma and metastatic malignant melanoma, without adverse side effects associated with the known treatments. The method comprises identification of in a patient one or more sentinel and/or metinel lymph nodes draining a malignant melanoma or a metastasis there from, resection of the one or more nodes and, optionally all or part of the tumour or metastasis, isolation of tumour-reactive T-lymphocytes from said lymph nodes, in vitro expansion of said tumour-reactive T-lymphocytes, and administration of the thus obtained tumour-reactive T-lymphocytes to the patient, wherein the T-lymphocytes are CD4+ helper and/or CD8+ T-lymphocytes.

23 Claims, 14 Drawing Sheets

OTHER PUBLICATIONS

Renkin, Am J Physiology, H706-H710 (1986).
35th Annual Meeting and 20th Summer School of the Scandinavian Society for Immunology, Aarhus, Denmark, Jun. 13-16, 2004, Scandinavian Journal of Immunology, 59(6):609-637 (Jun. 2004).
Chen et al, J. Experimental Medicine, 198:1875-1886 (2003).
Kursar et al, J. Experimental Medicine, 196:1585-1592 (2002).
Sutmuller et al, J. Experimental Medicine, 194:823-832 (2001).
Winter et al, Immunology, 108:409-419 (2003).
Gura, Science, 278:1041-1042 (1997).
Dahl, European Journal of Surgical Oncology, 31:381-385 (Jan. 28, 2005).
Saxton et al, Blood, 89:2529-2536 (1997).
Marincola et al, Trends in Immunology, 24(6):334-341 (2003).
Ruttinger et al, Clinical and Experimental Metastasis, 21:305-312 (2004).
Kim et al, Cancer, 86:22-30 (1999).
Hedfords et al, Scandinavian Journal of Immunology, 58:522-532 (2003).
Dillmon, Expert Review of Anti-Cancer Therapy, 5(6):1041, Abstract (2005).
Steven A. Rosenberg, et al. Prospective Randomized Trial of High-Dose Interleukin-2 Alone or in Conjunction with Lymphokine-Activated Killer Cells for the Treatment of Patients With Advanced Cancer. Journal of the National Cancer Institute, vol. 85, No. 8 Apr. 21, 1993. pp. 622-632.
Steven A. Rosenberg et al., Cancer regression in patients with metastatic melanoma after the transfer of autologous antitumor lymphocytes. PNAS. Oct. 5, 2004, vol. 101 Supp. 2, 14639-14645.www.pnas.org/cgi/doi/10.1073/pnas.0405730101.
Monica C. Panelli, et al. Expansion of Tumor-T Cell Pairs from Fine Needle Aspirates of Melanoma Metastases. FNA Biopsies of Melanomas. pp. 495-504.
Hiroshi Tanaka, et al. Depletionof CD4+CD25+ Regulatory Cells Augments the Generation of Specific Immune T Cells in Tumor-Draining Lymph Nodes. Journal of Immunotherapy vol. 25(3) Nov. 3, 2002:207-217.
Cynthia S. Chin et al., Sentinel Node Mapping Identifies Vaccine-Draining Lymph Nodes With Tumor-Specific Immunological Activity. Ann. Surg. oncol. vol. 9, No. 1, 2002. pp. 94-103.
Rudikoff et al, PNAS USA, 79:1979-1983 (1982).
Coleman et al, Research in Immunology, 145(1):33-36 (1994).
Burgess et al, Journal of Cell Biology, 111:2129-2138 (1990).
George et al, Trends in Immunology, 26(12):653-659 (2005).
Thorn et al, Cancer Causes control, 8(4):560-567 (1997).
Holmang et al, J. Urol. 158(2):389-392 (1997).
Sternberg, Annals of Oncology, 13:273-279 (2002).
Advanced Bladder Cancer Meta-Analysis Collaboration, Lancet, 361:1927-1934 (2003).
Bassi et al, J. Urol., 161(5):1494-7 (1999).
Cabanas, Cancer, 39:456-466 (1977).
Balch et al, J. Clin. Oncol., 19:3622-3634 (2001).
Sherif et al, J. Urol., 166(3):812-815 (2001).
Lipponen et al, Eur. J. Cancer, 29A(1):69-75 (1992).
Morales et al, J. Urol., 116(2):180-183 (1976).
Itano et al, Nature Immunology, 4:733-739 (2003).
Moll et al, Am. J. Pathol., 140(2):427-447 (1992).
Ochsenbein et al, Nature, 411:1058-64 (2001).
Velotti et al, J. Immunotherapy, 20(6):470-478 (1997).
Baner et al, Clin Chem, 51(4):768-775 (2005).
Haas et al, Cancer Immunol Immunother, 30(6):342-350 (1990).
Housseau et al, Int J Cancer, 71(4):585-594 (1997).
Dudley et al, J. Clin. Oncol., 23(10):2346-2357 (2005).
Nakagomi et al, Cancer Res, 53:5610-5612 (1993).
Finke et al, Cancer Res, 53(23):5613-5616 (1993).
Martis et al, European Urology, 49(14):59-70 (Nov. 14, 2005).
Sherif et al, European Urology, 50(1):83-91 (Jul. 2006).
Burnet, Prog Exp Tumor Res, 13:1-27 (1970).
Ratliff, J. Urol., 137(1):155-158 (1987).
Ratliff, J. Urol., 150(3):1018-1023 (1993).
Cohen et al, Urol Clin North Am, 19(3):421-428 (1992).

* cited by examiner

Start

CD8

End

METHOD FOR TREATING MALIGNANT MELANOMA

FIELD OF THE INVENTION

The invention relates to an immuno-therapeutically method for treating patients suffering from malignant melanoma, by administering expanded tumour-reactive CD4+ helper and/or CD8+ T-lymphocytes obtainable from one or more sentinel or metinel lymph nodes draining a malignant melanoma or a metastasis arising from malignant melanoma, wherein the T-lymphocytes are not CD4+ CD25+$^{Hi}$ lymphocytes, i.e. the present invention does not cover regulatory T-lymphocytes.

BACKGROUND OF THE INVENTION

Human melanoma represents the principal cause of death in patients with skin cancer in United States and Europe. Melanoma is estimated to be the fifth and seventh most common cancers in men and women, respectively, among new cases of cancer in the United States in 2004. An increase of more than 600% in the diagnosis of cutaneous cancer has been seen from 1950 to 2000.

Rational treatment strategies for stage I and II patients have developed to optimize survival and minimize treatment morbidities The immune system often appears informed about tumours, as shown by an accumulation of immune cells at tumour sites, which correlates with improved prognosis. Immuno competent cells respond to "danger" signals, which can be provided of growing tumours as a consequence of the genotoxic stress of cell transformation and disruption of the surrounding microenvironment. Under ideal conditions, these signals will induce inflammation, activate innate effector cells with antitumour activity, and stimulate professional antigen-presenting cells (APCs), particularly dendritic cells (DCs), to engulf tumour-derived antigens and migrate to draining lymph nodes to trigger an adaptive response by T and B lymphocytes. Thus, the immune system is capable of recognizing and eliminating tumour cells but unfortunately tumours often interfere with the development and function of immune responses. However, recent advances in cellular and molecular immunology suggest strategies, which may prevent antitumour responses. Briefly, the presence of a tumour indicates that the developing cancer was able to avoid detection or to escape or to overwhelm the immune response. Progressing tumours often exhibit strategies that promote evasion from immune recognition. Examples are physical exclusion of immune cells from tumour sites, poor immunogenicity due to reduced expression of major histocompatibility complex (MHC) or costimulatory proteins, and disruption of natural killer (NK) and natural killer T (NKT) cell recognition. Further, some tumours prevent triggering of an inflammatory response by secreting proteins such as interleukin 10 (IL-10) or vascular endothelial growth factor (VEGF) that interfere with DC activation and differentiation, or by blocking the production of proinflammatory molecules by increasing expression of the STAT3 protein. Even if a response is induced, tumour cells may escape elimination by losing targeted antigens, rendering tumour-reactive T cells anergic, inducing regulatory T cells, or specifically deleting responding T cells. The tumour that finally develops reflects selection of poorly immunogenic and/or immune-resistant malignant cells.

In the adjuvant setting, tumour immunotherapy offers an appealing alternative to traditional cytostatics. One strategy has been to expand and activate NK cells in vitro with out specific antigen by culture with IL-2 followed by infusion of large numbers of these NK cells back into patients alone or with high doses of IL-2. This approach, or administration of high doses of IL-2 to expand and activate NK cells entirely in vivo, has yielded antitumour activity and remission in a subset of patients (Rosenberg S A et al., J Natl Cancer Inst 85, 622, 1993). However, life-threatening toxicity often develops, largely due to the release of tumour necrosis factor (TNF) from activated NK cells.

Other attempts to stimulate the innate specific T cell immunity have been done by different types of vaccines. Promising results from animal studies entailed a study in which autologous tumour cells and an adjuvant immunomodulating agent, bacillus Calmette-Guérin (BCG) was given in combination several times to 98 patients with colorectal cancer in a prospectively randomized study. No statistically significant differences were detected in survival but maybe a small decrease in recurrence rate in stage II colon cancer patients.

Thus, it is obvious that there is still a need for an effective and at the same time safe treatment of malignant melanoma and metastases thereof.

DISCLOSURE OF THE INVENTION

Accordingly, the present invention discloses a new effective method for treating malignant melanoma and metastatic malignant melanoma, without adverse side effects associated with the known treatments.

Adoptive immunotherapy, i.e. collection and in vitro expansion of autologous tumour-reactive lymphocytes, followed by transfusion back to the patient has never been done for treating malignant melanoma. The present inventors described herein a very successful attempt to use sentinel or metinel node acquired lymphocytes for immunotherapy of malignant melanoma. In short, the tumour or metastasis draining lymph node(s) is identified by injection of a lymph node locator. The nodes contain T-lymphocyte clones that have been naturally activated against tumour-derived antigens in vivo. This specific T lymphocyte population is further expanded using an improved method for expansion of tumour-reactive T-lymphocytes, wherein specific culturing conditions have been determined and optimized, and wherein specific markers on the T-lymphocytes and in the culture medium are monitored throughout the expansion phase, in order to obtain high numbers of tumour-reactive T-lymphocytes in the shortest possible time span.

Accordingly, the present invention relates to a method for treating patients suffering from malignant melanoma, the method comprising
i) identifying in a patient one or more sentinel and/or metinel lymph nodes draining a malignant melanoma or a metastasis there from,
ii) resecting the one or more nodes and, optionally, all or part of the tumour or metastasis,
iii) isolating tumour-reactive T-lymphocytes from said lymph nodes,
iv) in vitro expanding said tumour-reactive T-lymphocytes,
v) administering the thus obtained tumour-reactive T-lymphocytes to the patient,
wherein the T-lymphocytes are CD4+ helper and/or CD8+ T-lymphocytes and not CD4+ CD25+$^{Hi}$ lymphocytes, i.e. the present invention does not cover regulatory T-lymphocytes.

Before going in to further details with the steps of the method of the invention, the following terms will be defined:
By the term "tumour-reactive T-lymphocytes" is intended to mean T-lymphocytes carrying a T cell receptor (TCR)

specific for and recognizing a tumour antigen. Herein the term tumour-reactive T-lymphocytes also tends to cover T-lymphocytes carrying a TCR specific for and recognizing metastasis antigens. I.e. the terms tumour-reactive T-lymphocytes and metastasis-reactive T-lymphocytes may be used interchangeable.

By the term "tumour-reactive T-lymphocytes" is intended to mean T-lymphocytes carrying a T cell receptor specific for and recognizing a tumour antigen.

By the term "T helper cells" is intended to mean T-lymphocytes that promote adaptive immune responses when activated.

By the term "Th1 cells" is intended to mean T helper cells that promote cell mediated immune responses when activated, using cytokines such as IFN-gamma.

By the term "Th2 cells" is intended to mean T helper cells promoting humoral immune responses when activated, using cytokines such as IL4.

By the term "CD4+ helper T-lymphocytes" is intended to mean T-lymphocytes that express CD4 but not the transcription factor FoxP3.

By the term "CD8+ T-lymphocytes" is intended to mean T-lymphocytes that express CD8.

By the term "regulatory T-lymphocyte" is intended to mean T-lymphocytes that suppress adaptive immune responses, expressing transcription factor FoxP3.

By the term "specific activation" of T-lymphocytes is intended to mean antigen specific and MHC restricted T-cell receptor mediated activation. In contrast the term "unspecific activation" of T-lymphocytes is intended to mean a general activation of all T-cells, regardless of T-cell receptor specificity.

The term "tumour-derived antigen" intends to cover tumour cells, a homogenate of a tumour, which homogenate may be denatured, or tumour proteins, polypeptides or peptides, e.g. in the form of purified, natural, synthetic and/or recombinant protein, polypeptide or peptide. The tumour-derived antigen may be intact molecules, fragments thereof or multimers or aggregates of intact molecules and/or fragments. Examples of suitable polypeptides and peptides are such that comprises from about 5 to about 30 amino acids, such as, e.g. from about 10 to 25 amino acids, from about 10 to 20 amino acids or from about 12 to 18 amino acids. If peptides are used, a final molar concentration in the culture of from about 0.1 to about 5.0 µM, such as, e.g., from about 0.1 to about 4.0 µM, from about 0.2 to about 3.0 µM, from about 0.3 to about 2.0 µM or from about 0.3 to about 1.0 µM may be used. The tumour-derived antigen may be autologous or heterologous, i.e. arise from the patient to be treated or be obtained from another subject suffering from cancer. In the present Examples the inventors uses an autologous denatured tumour extract, however, as mentioned above, other sources of the tumour-derived antigen may also be feasible for use in a method according to the invention.

By the term "day 1 of the first phase" or e.g. "day 5 of the second phase" is to be understood the following: The day on which the lymphocytes are harvested is denoted day 0 (zero). Day 1 of the first phase is defined as the day where the expansion is initiated by addition of at least one substance having agonistic activity towards the IL-2 receptor, and maybe culture medium and/or tumour-derived antigen. The expansion phase i) may be initiated on day 0 (zero) or up till 2 days after harvest of the lymphocytes. The day on which the second phase is initiated by addition of tumour-derived antigen is throughout the text described as "day 1 of the second phase".

By the term "sentinel lymph node" is intended to mean the first lymph node(s) to receive lymphatic drainage from a tumour. Primary tumours or primary tumour areas drain to one or more so-called sentinel lymph nodes. The sentinel nodes are also the first site of metastasis and it has been shown in several solid tumour types that the risk of lymph node metastases is almost negligible if the sentinel node is free of tumour cells. The term "metinel lymph node" refers to the first lymph node(s) to receive lymphatic drainage from a metastasis or a metastases area.

The term "malignant melanoma" embraces any stage including stage I, II, III and IV and substages thereof. A person skilled in the art will know that dependent on the specific stage of the disease a specific treatment regimen may be necessary such as, e.g., further administration of the lymphocytes obtained as described herein and/or relevant combination treatment with drugs normally used for the treatment of malignant melanomas or metastasis thereof. Furthermore, it is contemplated that variation of the expansion method may depend on the stage of the malignant melanoma. The method given herein is a general method that normally is regarded as applicable for any stage, however, some optimization may be needed for the specific stage.

The first step in the present method is the identification of one or more sentinel or metinel lymph nodes draining a malignant melanoma or a metastasis there from. The step i) of identifying one or more sentinel or metinel nodes are crucial for the method according to the invention, as the present inventors have shown that these nodes comprises a high amount of T-lymphocytes activated against tumour-derived antigens in vivo.

One way of identifying the sentinel or metinel lymph node is by injecting one or more lymph node locators into the patient, i.e. any substances suitable for locating a lymph node. Such locators are preferably pharmaceutically acceptable and/or biocompatible. The locators can either be affinity based or non-affinity based. Examples of affinity based lymph node locators are antibodies in whole or fragments, nanobodies, nucleic acids such as RNA, DNA, and PNA all of which can be in turn labelled using various detection modalities. Detection of affinity based lymph node locators can be done by labeling with tracers and dyes, such as, e.g., the ones mentioned below. Visualization is then made by i) radiological methods such as x-ray, computerized tomography, scintigraphy, positron emission technique after labelling with contrast generating substances, such as, e.g., iodine containing substances or radioactive substances such as, e.g. technetium-99m, ii) magnetic resonance imaging after labelling with magnetic or paramagnetic substances, such as e.g., gadolinium, magnetodendromers or iron oxide containing particle; iii) light in the IR-visible-UV spectra by labelling with dyes, fluorescent dyes or luminescent dyes for detection by the naked eye or photon detecting devices such as CCD or CMOS sensors.

Examples of non-affinity based lymph node locators encompass tracers and dyes. These substances are transported in the lymph capillaries and accumulate through phagocytosis by macrophages in the sentinel or metinel node(s), thus identifying the tumour or metastasis draining lymph node(s).

Examples of tracers are radioactive substances such as, e.g., technetium-99 for radioactive decay based detection with photon sensitive films or sensors such as PET detectors. Further on magnetic, paramagnetic or superparamagnetic substances, such as, e.g., gadolinium containing contrast agents, iron oxide particles, magnetic oxide particles, magnetodendrimers for magnetic resonance based detection, contrast agents, such as, e.g., iodine for radiological based detection such as, e.g., computerized tomography or regular X-ray may be used.

Examples of dyes encompasses e.g., azo dyes, bisazo dyes, triazo dyes, diaryl methan dye, triaryl methan dye, anthrachino dye, polycyclic aromatic carbonyl dyes, indigo dyes for visualization by luminescence, near infrared, fluorescence, UV and visible light. Further on dyes also encompass luminescent substances for luminescence based detection and fluorescent substances, such as, e.g., pico green, sybr green, red O oil, texas red for fluorescence based detection. Detection can depending on the chosen wavelengths be made either by the naked eyes or photon detecting devices such as CCD or CMOS sensors.

In one embodiment the dye has an emission maximum that permits visualization by the naked eye in normal light. In another embodiment the dye has an emission maximum that permits visualization by the naked eye in UV light.

Other examples of suitable dyes or tracers appear from WO 04/045650, which is hereby incorporated by reference.

Another, but far more time-consuming way to identify sentinel or metinel nodes is to remove and investigate a selection of lymph nodes in the presumed tumour or metastasis area. A tumour extract from the tumour or metastasis of the actual patient could then be used to identify lymph nodes containing tumour-reactive T-lymphocytes by proliferating assays.

The lymph node locators are injected into the patient into, above, around, adjacent and/or under the tumour or metastasis. The locator will then spread through lymph vessels leading into the metinel lymph node(s), and the one or more nodes will start to get stained within a certain period of time, such as, e.g. within 5 min to 30 min, such as, e.g. within 5 min to 15 min after injection of the locator substance, where after the locator substance is imaged. As described above, imaging of the locator is of course dependent on the locator substance used.

If a dye having an emission maximum that allows visualization by the naked eye in normal light is used, such as, e.g. Patent Blue, the one or more sentinel or metinel nodes are simply identified as the nodes, which are first to accumulate the coloured dye, i.e. if Patent Blue is used, the surgeon will look for the lymph nodes first to accumulate a blue colour.

The locators may be injected by a single injection or by multiple injections, such as, e.g., by two or more injections, by three or more injections, by four or more injections, by five or more injections or by six or more injections.

How to perform the injections of the lymph node locators is dependent on the location of the tumour or metastasis.

In case of a malignant melanoma, the lymph node locators may be injected involving a surgical procedure, i.e. a procedure that includes an incision. In such cases, the surgeon will perform an incision in the area of the tumour and subsequently, a lymph node locator may be injected directly into, above, around, adjacent and/or under the metastasis in order to identify the one or more sentinel lymph nodes. The lymph node locators may also be injected by a non-surgical procedure, i.e. a procedure that does not involve a surgical step, wherein a surgical step is defined a one including surgical operative procedures, i.e. involving incisions with an instrument. In the present context, an injection, i.e. the punctuation of the skin with a needle, is not considered a surgical step. Accordingly, by the statement that the lymph node locator may be injected by a non-surgical procedure is intended to mean that the lymph node locator may be injected into, above, around, adjacent and/or under the metastasis directly into or through the skin.

Examples of situations wherein the lymph node locators may be injected into or through the skin, is e.g. cases where metastasis of malignant melanomas are located in the skin of the patient. In such situations the lymph node locator should preferentially be injected into the skin above the metastasis, or through the skin into, around, adjacent and/or under the metastasis. If the metastasis is located in the breast area of the patient, the lymph node locator should preferentially be injected into the skin above the metastasis, or through the skin into, around, adjacent and/or under the metastasis.

In case of a metastasis of a malignant melanoma, the metinel lymph nodes may not always be placed at the shortest or most logical anatomical distance from the metastasis. Accordingly, as a metinel lymph node may be placed distant from the metastasis, it may in some cases be very beneficial to inject a lymph node locator without the need for surgery, as it may be very difficult to predict the position of such a metinel lymph node, and there by difficult to predict the place in the body to perform the surgery to remove the metinel node. In a specific embodiment of the invention, the lymph node locator is a radioactive substance, such as, e.g. technetium-99m, which may be injected by a non-surgical procedure, and later imaged by performing a lymphoscintigraphy.

Some times the identification of the metinel lymph nodes may involve injection of lymph node locators by a combination of a non-surgical and a surgical step. As an example of this a radioactive lymph node locator, such as, e.g., technetium-99m may be injected using a needle, i.e. without the need for surgery, and the accumulation of the locator, i.e. identification of the metinel node(s) may be performed using a gamma detector. This gives the surgeon an indication towards where the metinel nodes are located. Later on, when the patient is undergoing surgery to have the metinel lymph nodes and at least part of metastasis removed, a coloured dye such as, e.g., Patent Blue Dye may be injected. Furthermore, if there is a lapse of more than about 18 to 24 hours after the first injection, it might be beneficial to add one or more extra injections with radioactive tracer dependent on the half-life of the radioactive tracer (usually about 6 hours) in order to identify the metinel nodes during surgery.

After having located the one or more sentinel or metinel lymph nodes by one or the other method, the surgeon will remove these in order to investigate whether the sentinel or metinel lymph nodes contain any tumour cells, and in order to obtain a culture of tumour-reactive T-lymphocytes.

The harvesting of lymphocytes from the one or more sentinel or metinel lymph nodes may be performed by homogenizing the sentinel or metinel lymph node material in order to obtain single cell suspensions of lymphocytes. The single cell suspensions may then be subjected to in vitro expansion in order to obtain tumour-reactive T-lymphocytes.

In vitro Expansion

The in vitro expansion step iv) of the method according to the invention comprises i) a first phase of stimulating tumour-reactive CD4+ helper and/or CD8+ T-lymphocytes with tumour-derived antigen together with at least one substance having agonistic activity towards the IL-2 receptor, to promote survival of tumour-reactive CD4+ helper and/or CD8+ T-lymphocytes, and ii) a second phase of activating and promoting growth of tumour-reactive CD4+ helper and/or CD8+ T-lymphocytes, wherein the second phase ii) is initiated when the CD25 cell surface marker (IL-2R marker) is down-regulated on T-lymphocytes.

Phase i)

The purpose of the first phase i) is to obtain a culture comprising a substantially high ratio of tumour-reactive CD4+ helper and/or CD8+ T-lymphocytes. The first phase is to be considered a "nursing phase" where the tumour-reactive T-lymphocytes are brought to survive and divide. Depending on the source of the T-lymphocytes (starting material for the in vitro expansion method), they may have phased relatively harsh conditions, such as, e.g., suppression and inhibition by factors secreted by cancer cells.

The starting material for use in the expansion method may be a mixture of lymphocytes and antigen presenting cells obtained from lymph nodes draining a metastasis.

The T-lymphocytes to be expanded in culture can be obtained from the subject to be treated, i.e. the resulting specific tumour-reactive T-lymphocytes for administering may be autologous. However, the T-lymphocytes can also be obtained from a source other than the subject to be treated, such as, e.g. another subject suffering from a cancer. In such case the recipient and the expanded tumour-reactive T-lymphocytes are preferably immunologically compatible (or the recipient is otherwise made immuno-tolerant of the expanded tumour-reactive T-lymphocytes).

The starting material will most likely comprise a mixture of various lymphocytes, such as, e.g., T-lymphocytes, B-lymphocytes, antigen presenting cells, tumour-reactive T-lymphocytes and non-activated/non-reactive T-lymphocytes. In order to promote survival specifically of the tumour-reactive T-lymphocytes, tumour-derived antigen and one or more substances having agonistic activity towards the IL-2 receptor are added.

As mentioned above the first phase i) is initiated by adding at least one substance having agonistic activity towards the IL-2 receptor. The function of such substances is to stimulate T-lymphocytes via the IL-2 receptor to promote cell division of T-lymphocytes, thereby preventing cell death.

Antigen specific MHC restricted activation of T-lymphocytes promotes clonal expansion of the useful T-lymphocyte population specific for the recognition of tumour cells. On the contrary, unspecific activation of T lymphocytes will lead to the expansion of T lymphocyte clones recognizing irrelevant peptides without any relation to the recognition of tumour cells, thus the majority of unspecifically expanded T lymphocytes will not recognize the tumour.

The invention aims to promote specific activation and growth of tumour-reactive CD4+ helper and CD8+ T-lymphocytes. A specific activation against a certain tumour antigen enables the T-lymphocytes to have therapeutic effect when administered to a cancer patient with the same tumour type as the T-lymphocytes are activated against.

In one embodiment of the invention the substances having agonistic activity towards the IL-2 receptor are agonists. Examples of such substances include proteins, polypeptides, peptides, antibodies, affibodies, and fragments thereof, fusion proteins, synthetic and/or organic molecules, such as, e.g., small molecules, and natural ligands. In a preferred embodiment the substance is the natural ligand of the IL-2 receptor, namely IL-2.

If IL-2 is used it is preferentially added in a low dose in order to reduce lymphocyte apoptosis and to increase the population of CD4 positive tumour-reactive T-lymphocytes. In a specific embodiment of the invention, the low dose of IL-2 is from about 100 IU/ml culture medium to about 700 IU/ml culture medium, such as, e.g., from about 100 IU/ml culture medium to about 600 IU/ml culture medium, from about 100 IU/ml culture medium to about 500 IU/ml culture medium, from about 100 IU/ml culture medium to about 400 IU/ml culture medium, from about 100 IU/ml culture medium to about 300 IU/ml culture medium and from about 100 IU/ml culture medium to about 200 IU/ml culture medium. In a specific embodiment, the amount of IL-2 added is 240 IU/ml.

In case other substances, than IL-2, having agonistic activity towards the IL-2 receptor are used the specific doses of these should be such that lead to an effect corresponding to the effect obtained by the above-mentioned doses of IL-2.

A further amount of the at least one substance having agonistic activity towards the IL-2 receptor may be added regularly throughout phase i), such as, e.g., every $2^{nd}$, $3^{rd}$ or $4^{th}$ day of phase i), in order to maintain optimal conditions for promoting cell division. By the term every $2^{nd}$, $3^{rd}$ or $4^{th}$ is intended to mean that at least one substance having agonistic activity towards the IL-2 receptor is added throughout phase i) every $2^{nd}$, $3^{rd}$ or $4^{th}$ day, starting at the $2^{nd}$, $3^{rd}$ or $4^{th}$ day after the first addition of the at least one substances having agonistic activity towards the IL-2 receptor, i.e. after initiating phase i).

In one embodiment the substance to be added regularly throughout phase i) is an agonist of IL-2. In a preferred embodiment the substance is IL-2.

The further dose of substances having agonistic activity towards the IL-2 receptor, such as, e.g., IL-2, to be added regularly, such as, e.g. every $2^{nd}$, $3^{rd}$, or $4^{th}$ day lies within the ranges mentioned above.

A further important step in the first phase i) of expansion is the addition of tumour-derived antigen in order to promote cell division of T-lymphocytes expressing T lymphocyte receptors recognizing tumour antigens, i.e. tumour-reactive T-lymphocytes.

The optimal point of time to add the tumour-antigen is depending on the source of lymphocytes. When the lymphocytes originates from lymph nodes the lymphocytes may have been subjected to close proximity and immuno-suppression by tumour cells, and need incubation with a substance having agonistic activity towards the IL-2 receptor, such as, e.g., IL-2 for some days in order to promote the ability of the T-lymphocytes to respond with proliferation upon tumour antigen presentation. Accordingly, in such case the tumour-derived antigen is preferentially added from day 2 to and including day 5 of the first phase i), such as, e.g., on day 2, on day 3, on day 4 or on day 5.

The tumour-derived antigen, such as, e.g., a tumour homogenate, is likely to be endocytosed and processed by antigen presenting cells present in the starting material, such as, e.g., B-lymphocytes, dendritic cells and macrophages. In most cases the tumour-derived antigen will be presented by class II MCH molecules leading to cell division of $CD4^+$ tumour-reactive T-lymphocytes. However, by cross presentation antigens taken up by endocytosis may be processed and presented in the class I pocket resulting in activation of $CD8^+$ T lymphocytes. As stated above, one of the objects of the expansion method is to in some respect imitate the natural pathway of the patients own immune system, and to a certain degree let the components of the patients immune system determine whether $CD4^+$ or $CD8^+$ lymphocytes are generated, depending on whether antigen is presented by MCHI or MCHII. In most cases, the antigens will be presented by the class II MCH molecule leading to generation of $CD4^+$ T-lymphocytes, however, in some cases $CD8^+$ T-lymphocytes are generated.

Phase ii)

The purpose of the second phase ii) is to activate and expand the tumour-reactive CD4+ helper and/or CD8+ T-lymphocytes obtained by phase i) and to obtain a specific sub-population of tumour-reactive CD4+ helper and/or CD8+ T-lymphocytes by directing them into a desired pathway.

The present inventors have found, that one way of determining the optimal point in time to initiate phase ii) is by monitoring the expression of the CD25 cell surface marker on the T-lymphocytes, in order to determine specifically when the T-lymphocytes are susceptible to re-stimulation. The present inventors have found that the second phase ii) should preferably be initiated when the expression of CD25 on T-lymphocytes is down-regulated. CD25 is an activation marker, indicating that the lymphocytes have received an activating signal. If the second phase is initiated when the expression of CD25 on the T-lymphocytes is high, meaning that the lymphocytes have already received a signal, cell death would occur.

The down-regulation of CD25 is defined as that a substantial part of the T-lymphocyte population express very few or essentially none CD25 markers. In a preferred embodiment the down-regulation of CD25 is defined as that less than 5% of the T-lymphocyte population expresses CD25, i.e. 95% or more of the T-lymphocytes in the culture does not express CD25 at all. The 5% or less of the T-lymphocytes expressing CD25 is most likely regulatory CD4+ T-lymphocytes which have a high permanent expression of CD25. In addition the T-lymphocyte population should preferably express very few or essentially none FoxP3 markers, which are specific markers of regulatory T-lymphocytes. In a preferred embodiment the down-regulation of FoxP3 is defined as that less than 5% of the T-lymphocyte population expresses FoxP3, i.e. 95% or more of the T-lymphocytes in the culture do not express FoxP3 at all.

Besides CD25, there are also other markers, the expression of which is relevant to monitor in order to determine the optimal point in time to initiate the second phase.

Examples of such markers are the early activation marker CD69, and MCHII, which is an activation marker for T-lymphocytes. As the expression of CD69 and MCHII indicates that the "activation program" of the T-lymphocytes is already turned on, meaning that the cells are not able to respond to additional stimuli, both of these markers should preferably be down-regulated before the second phase is initiated. The term down regulation may be defined as that less than 5-10% of the T-lymphocyte population expresses CD69 and/or MCHII.

In another embodiment of the present invention, anti-CD4 antibodies are used to separate T helper cells from possible tumour cells in the culture in the expansion in phase ii) of the expansion method.

In a further or yet another embodiment of the present invention, products such as Dynabeads® with anti-CD3 and anti-CD28 antibodies are used to promote the expansion in phase ii) of the expansion method. Use of Dynabeads® CD3/CD28 will provide lymphocytes with activation signals and could also be used for separation from possible tumour cells in the culture. Dynabeads® CD3/CD28 will bind to T lymphocytes expanded antigen specifically during phase i), where these cells now can be enriched magnetically. Since the initial antigen specific activation has initiated and led to clonal T lymphocyte expansion the Dynabeads® CD3/CD28 restimulation will further promote clonal expansion since phase i) does not support activation of unspecific T lymphocyte clones.

Even though the exact starting point of phase ii) will vary depending on when the lymphocytes has acquired the preferred expression of specific markers, the second phase ii) is most often initiated from day 17 to and including day 23 of the first phase i), such as, e.g. on day 17, on day 18, on day 19, on day 20, on day 21, on day 22 or on day 23. In other words, the point in time, where the lymphocytes expresses the preferred amount and combination of markers, is most often seen as being from day 17 to day 23 of the first phase i).

The expansion of the T-lymphocytes, i.e. phase i) and ii) will most often take place in a suitable culture medium. Preferably a serum-free medium or autologous serum is used in order to avoid the risk of transmitting diseases to the patient. Examples of suitable standard media include AIMV medium, RPMI 1640, DMEM and MEM. However, other media may also be used, comprising a suitable blend of amino acids, steroids, vitamins, growth factors, cytokines and minerals.

During the two phases of the expansion, the cells may be split into several culture vessels in order to maintain a suitable cell density in the cultures. The density of the T-lymphocytes in the expansion phases should preferably be from about 3 to about 6 million cells/ml of culture medium.

During expansion an exchange of culture medium with fresh medium, a step, which is denominated conditioning of the medium, may also be needed. The point of time to split cultures and to condition the medium may be determined based on the morphology of the cells and the cell culture density (which should not exceed about 6 million cells/ml), or the medium may contain a suitable indicator, such as, e.g., a phenol indicator. In case an indicator is included in the medium, the point of time to split cultures or condition medium may be based on the color of the medium. If a phenol red indicator is used, the cells should be split or conditioned, when the medium turns yellow, indicating that the pH of the culture is turning acidic. A suitable schedule for conditioning the medium used in the present invention may be to exchange from ¼ to ½, such as, e.g., ⅓ of the medium every 3-9 days, such as, e.g. once a week.

Except for the specific conditions mentioned herein, for other parameters standard conditions for growth of lymphocyte cultures will be used, such as, e.g. a temperature of 37° C. and 5% $CO_2$.

As mentioned above, the second phase ii) is initiated by the addition of tumour-derived antigen as defined above to the T-lymphocytes for activating the tumour-reactive CD25-negative T-lymphocytes, in order to promote clonal expansion of tumour-reactive T-lymphocytes.

In a specific embodiment of the invention antigen presenting cells (APCs) are added to the T-lymphocytes together with the tumour-derived antigen. Antigen presenting cells (APCs) include leukocytes such as, e.g., monocytes, macrophages and lymphocytes, such as, e.g., B cells. These diverse cell types have in common the ability to present antigen in a form that is recognized by specific T lymphocyte receptors. The leukocyte preparation is isolated from, for example, blood, lymph fluid, bone marrow, lymphatic organ tissue or tissue culture fluid obtained from the patient to be treated. In a preferred embodiment the APCs cells are irradiated peripheral blood leucocytes containing antigen-presenting B-cells and/or monocytes. The amount of APCs added lies within the range of from about 0.5 million APCs/ml lymphocyte culture to about 5 million APC/ml lymphocyte culture, such as, e.g., from about 1 million APCs/ml lymphocyte culture to about 4 million APC/ml lymphocyte culture, from about 1 million APCs/ml lymphocyte culture to about 3 million APC/ml lymphocyte culture, or from about 1 million APCs/ml lymphocyte culture to about 2 million APC/ml lymphocyte culture.

Besides the addition of tumour-derived antigen to the T-lymphocytes in order to promote clonal expansion of tumour-reactive T-lymphocytes, the second phase ii) comprises the addition of specific components the function of which are to direct the expansion of the tumour-reactive T-lymphocytes towards the desired sub-population.

As mentioned above, the present invention provides a method for the generation of tumour-reactive CD4+ helper T-lymphocytes. CD4+ helper T-lymphocytes recognizes and binds tumour antigen when the antigen is associated with a major histocompatibility complex class II molecule. Activated helper CD4+ T lymphocytes secrete cytokines, proteins and/or peptides that stimulate other cells of the immune system, such as other lymphocytes. The most common cytokine secreted is interleukin-2 (IL-2), which is a potent T lymphocyte growth factor. Activated, proliferating CD4+ helper T-lymphocytes can differentiate into two major subtypes of cells, Th1 and Th2 cells, which are defined on the basis of specific cytokines produced. Th1 cells produce interferon-gamma and interleukin 12 (IL-12), while Th2 cells produce interleukin-4, interleukin-5 and interleukin-13. Th1 T-lymphocytes are believed to promote activation of cytotoxic T lymphocytes (Tc), NK cells, macrophages, and monocytes, all of which can attack cancer cells and generally defend against tumours.

T-helper (CD4+) lymphocytes of type Th1 and Th2 can differentiate into memory cells and effector cells. Memory T-helper (CD4+) lymphocytes are specific to the antigen they first encountered and can be called upon during a secondary immune response, calling forth a more rapid and larger response to the tumour-antigens. There is evidence in humans that lymphocytes survive at least 20 years; perhaps for life. Effector CD4+ T-lymphocytes are active cells producing cytokines and INF-gamma.

For an effective treatment of cancer, administration of tumour-reactive T-lymphocytes of the Th1 type is especially beneficial, as this type is believed to promote activation of cytotoxic T lymphocytes (Tc), NK cells, macrophages, and monocytes, all of which can attack cancer cells and generally defend against tumours. I.e. in a specific embodiment the invention relates to a method for generating tumour-reactive CD4+ T-lymphocytes, and in a further embodiment, the percentage of T-lymphocytes of the Th2 type generated by the present method is 30% or less, such as, e.g., 25% or less, 20% or less, 15% or less, 10% or less, 5% or less or 0%, i.e. at least 70% of the tumour-reactive CD4+ T-lymphocytes are of the Th1 type, such as, e.g. at least 75%, at least 80%, at least 85%, at least 90%, at least 95% or 100%.

Accordingly, the second phase may comprise the addition of a substance capable of up-regulating IL-12R on the T-lymphocytes. Up regulation of the IL-12R will increase the readiness of the T cell to receive and optimize the IL-12 cytokine activation resulting in maximal STAT-4 signaling and thus skewing the lymphocytes towards Th1 cells and IFN-γ production.

The substance(s) capable of up-regulating IL-12R on the T-lymphocytes may be substance(s) having agonistic activity towards an interferon receptor. In one embodiment of the invention the substances having agonistic activity towards the interferon receptor are agonists. Examples of such substances include proteins, polypeptides, peptides, antibodies, affibodies, and fragments thereof, fusion proteins, synthetic and/or organic molecules, such as, e.g., small molecules, and natural ligands. In a specific embodiment the substance is the natural ligand of the interferon receptor, namely an interferon, such as interferon-α.

The optimal point of time to add the substance(s) capable of up-regulating IL-12R on the T-lymphocytes, such as, e.g. a substance having agonistic activity towards an interferon receptor may be determined by measuring the level of IL-12 in the culture medium. The substance(s) should preferably be added when the level of IL-12 is at least 1 fold, such as, e.g., at least 2, at least 3 fold, at least 4 fold, or at least 5 fold increased as compared to the level of IL-12 on day 1 of phase ii). In most cases, such an increase in the level of IL-12 will be seen from day 2 to and including day 4 after initiating the second phase ii), such as, e.g. on day 2, on day 3 or on day 4.

In order to substantially avoid the generation of tumour-reactive T-lymphocytes of the Th2 type, the second phase may further comprise the addition of one or more substances capable of antagonizing development of Th2 type T-lymphocytes. Examples of such substances are substances capable of neutralizing the interleukins IL-4, IL-5, IL-10, and/or TGF-beta (the latter not being an interleukin) all four of which are required for the establishment of the Th2 cytokine profile and for down regulation of Th1 cytokine production.

Examples of such substances include proteins, polypeptides, peptides, soluble receptors, antibodies, affibodies, and fragments thereof, fusion proteins, synthetic and/or organic molecules, such as, e.g., small molecules, and natural ligands. In a specific embodiment the substances are selected from antibodies that binds to the interleukins, thereby neutralizing them, such as, e.g. anti IL-4 antibody, anti IL-5 antibody and/or anti IL-10 antibody, together with soluble receptors (such as, e.g. TGF-beta receptor I and II) and binding proteins for TGF-beta (such as, e.g. LAP and/or LTBP).

The one or more substances capable of antagonizing development of Th2 type T-lymphocytes, such as, e.g., one or more substances capable of neutralizing IL-4, IL-5, IL-10 and/or TGF-beta may be added on day 1 of the second phase ii). However, as antibodies are expensive, the addition of antibodies can also be performed in a subsequent step after addition of the substance capable of up-regulating IL-12R on the T-lymphocytes, such as, e.g., one day, two days or three days after addition of the substance capable of up-regulating IL-12R on the T-lymphocytes.

The neutralizing substances should be added in an amount sufficient to neutralize the interleukins, such as, e.g., in a 10-100 fold (molar) excess of the amount of interleukin to be neutralized. When using antibodies, a final concentration of from about 2 to about 4 ng/ml culture medium will normally be needed. For other types of neutralizing substances, a final concentration, giving the same effect as the concentration mentioned for antibodies, should be used.

In order to maintain the suppression of the development of Th2 type T-lymphocytes a further amount of the one or more substance capable of antagonizing development of Th2 type T-lymphocytes, such as, e.g., one or more substance capable of neutralizing IL-4, IL-5, IL-10 and/or TGF-beta may be added regularly throughout phase ii), such as, e.g. every $2^{nd}$, $3^{rd}$ or $4^{th}$ day of phase ii). It is to be understood that by the term every $2^{nd}$, $3^{rd}$ or $4^{th}$ is intended to mean that at least one substance capable of antagonizing development of Th2 type T-lymphocytes is added throughout phase i) every $2^{nd}$, $3^{rd}$ or $4^{th}$ day, starting at the $2^{nd}$, $3^{rd}$ or $4^{th}$ day after the first addition of the at least one substance capable of antagonizing development of Th2 type T-lymphocytes.

Furthermore, as for phase i) a further amount of a substance having agonistic activity towards the IL-2 receptor, such as, e.g., an agonist may be added regularly throughout phase ii) such as, e.g., every $2^{nd}$ to $4^{th}$ day of phase ii), i.e. on the $2^{nd}$, $3^{rd}$ or $4^{th}$ day in order to maintain optimal conditions promoting cell division. The dose of the substance to be added regularly lies within the optimal ranges mentioned under phase i) for addition of substances having agonistic activity towards the IL-2 receptor, such as, e.g., IL-2.

In order to favor the generation of Th1 type tumour-reactive T-lymphocytes, the second phase ii) may comprise adding one or more substances promoting the development of Th1 type T-lymphocytes. Examples of such substances are substances having agonistic activity towards the IL-7, IL-12, IL-15 and/or IL-21 receptor. More specific, the substances may be agonists for the IL-7, IL-12, IL-15 and/or IL-21 receptor. Examples of such agonists include proteins, polypeptides, peptides, antibodies, affibodies, and fragments thereof, fusion proteins, synthetic and/or organic molecules, such as, e.g., small molecules, and natural ligands. In a specific embodiment the substances are the natural ligands of the IL-7, IL-12, IL-15 and/or IL-21 receptor, respectively, such as IL-7, IL-12, IL-15 and/or IL-21.

The effect of IL-12 is activating the IFN-gamma inducing STAT pathway by stimulating the IL-12R thereby promoting activation of Th1 lymphocytes. The function of IL-21 is to enhance proliferation, activation and development towards a Th1 type of T-lymphocytes.

Both IL-7 and IL-15 work by promoting homeostatic expansion of the T-lymphocytes, enhancing the enumeration of activated Th1 programmed T-lymphocytes.

The optimal point of time to add one or more substances promoting development of Th1 type T-lymphocytes is when the T-lymphocytes are susceptible to modification. If the substances are added when the T-lymphocytes are not susceptible to modification, the addition will have no effect, i.e. the development of Th1 type T-lymphocytes will not be favoured. In order to determine the optimal point in time for adding substances promoting development of Th1 type T-lymphocytes, such as, e.g., substances having agonistic activity towards the IL-7, IL-12, IL-15 and/or IL-21 receptor, the production of INF-γ by the T-lymphocytes, may be monitored. In a preferred embodiment, the one or more substances promoting the development of Th1 type T-lymphocytes, such as, e.g., substances having agonistic activity towards the IL-7, IL-12, IL-15 and/or IL-21 receptor should be added when the level of IFN-gamma is increased as compared to the level of IFN-gamma on initiation of second phase ii).

In a specific embodiment, the increase in IFN-gamma level may be determined as at least a 1 fold increase in IFN-gamma level, such as, e.g., at least a 2 fold, at least a 3 fold, at least a 4 fold increase as compared to the level of IFN-gamma on initiation of the second phase ii). Often will such an increase can be correlated to that the content IFN-gamma in the culture medium should be at least 100 picogram/ml culture medium, such as, e.g. at least 150 picogram/ml culture medium, at least 200 picogram/ml culture medium or at least 250 picogram/ml culture medium.

When determining the optimal point in time to add substances promoting development of Th1 type T-lymphocytes, such as, e.g., substances having agonistic activity towards the IL-7, IL-12, IL-15 and/or IL-21 receptor, one may further look at the expression of the activation markers CD25 and CD69 on CD4+ T-lymphocytes, which markers should preferentially be up-regulated. By up-regulation is understood that at least about 40% to about 60% or more of the CD4+ T-lymphocytes should express CD25 and CD69 as compared to the expression of CD25 and CD69 on T-lymphocytes on day 1 of phase ii), showing that the T-lymphocytes have received an activating signal.

Normally, the optimal point of time for adding the substances promoting development of Th1 type T-lymphocytes will fall subsequent to the steps of adding the substances capable of up-regulating IL-12R on the T-lymphocytes and the substances capable of antagonizing development of Th2 type T-lymphocytes. More specific the optimal point in time to add the substances promoting development of Th1 type T-lymphocytes will fall between day 5 to day 8 after initiating the second phase ii), such as, on day 5, day 6, day 7 or day 8.

In case IL-7, IL-12, IL-15 and/or IL-21 are added the concentration of each of these substances in the culture medium should lie within the range from about 150 IU/ml culture medium to about 300 IU/ml culture medium, such as, e.g. 250 IU/ml culture medium. When other substances than the specific ones mentioned is used, they should be added to the culture in final concentration, which leads to the same effect as the addition of IL-7, IL-12, IL-15 and/or IL-21 within the specific ranges mentioned will give.

As mentioned above, the present method if preferentially used for the expansion of T-lymphocytes in order to achieve CD4+ tumour-reactive T-lymphocytes of the Th1 type. One further aspect of the invention is that by using the method described herein for expanding tumour-reactive T-lymphocytes, a relatively high amount of T-lymphocytes of the memory type will be obtained. In treating cancer it is of course important that the patient to be treated receive a high amount of effector tumour-reactive CD4+ T-lymphocytes, as these—as mentioned above—promote activation of cytotoxic T lymphocytes (Tc), NK cells, macrophages, and monocytes, all of which can attack cancer cells and generally defend against tumours.

However, by at the same time administering a substantial amount of memory tumour-reactive CD4+ T-lymphocytes, the patient achieve up to life long protection towards recurrence of the tumour or metastasis of the primary tumour.

Accordingly, the present invention relates to a method for the preparation of memory T-lymphocytes. Normally, when a culture of tumour-reactive T-lymphocytes are expanded according to the present invention from about 35% to about 90% of tumour-reactive T-lymphocytes of the memory type, such as, e.g. from about 40% to about 90%, from about 50% to about 80% or from about 60% to about 70%, will be obtained. The present inventors speculates that the fact that the lymphocytes in phase i) are allowed to regenerated before tumour antigen is added, together with the relatively slow expansion phase leads to formation of a high ratio of memory lymphocytes to effector lymphocytes.

As mentioned above the expression of the cell surface activation markers CD25 and CD69 on the T-lymphocytes may be used for determining when to initiate important steps of the present method, such as, e.g., when to initiate the second phase ii). Accordingly, it may be beneficial to continuously monitor the expression of CD25 and CD69 throughout phase i) and phase ii), such as, e.g., every $2^{nd}$, every $3^{rd}$ or every $4^{th}$ day.

As one of the purposes of the present method is to obtain a high number of specific CD4+ tumour-reactive T-lymphocytes, which may be used for administering to a patient, the tumour-reactive T-lymphocytes may be harvested at some point, leading to the termination of the expansion step. The optimal point of time to harvest the tumour-reactive T-lymphocytes is when the expression of CD25 on the T-lymphocytes is down-regulated, where the down-regulation is defined as that 5% or less of the CD4+ T-lymphocyte population expresses CD25. The optimal point in time to harvest may also be determined based on measurement of the amount of IFN-gamma produced. The IFN-gamma production should be at least 2 fold increased, such as, e.g., at least 3 fold, at least 4 fold or at lest 5 fold increased as compared to initial IFN-gamma production, which normally correspond to a level of IFN-gamma of at least 100 pg/ml of culture medium.

Normally, this event will occur from day 10 to and including day 14 after initiating the second phase ii), i.e. normally the cells will be harvested from day 10 to and including day 14 after initiating the second phase ii).

Accordingly, the entire process for expansion of tumour-reactive T-lymphocytes according to the invention may in general take from about 25 days to and including about 45 days, such as, e.g. from about 26 days to and including about 44 days, from about 27 days to and including 43 days, from about 27 days, to and including 42 days, from about 27 days to and including 41 days, and from about 27 days to and including about 40 days.

Instead of harvesting the tumour-reactive T-lymphocytes when the CD25 marker is down regulated, they may be subjected to one or more additional rounds of phase ii). This could be beneficial to do if the amount of tumour-reactive T-lymphocytes obtained by the expression method is not considered an effective amount to be administered to a patient suffering from cancer, or if the patient is in a chemotherapy treatment regimen, where it may be considered beneficial to postpone the administration of T-lymphocytes until the chemo-therapy treatment is finished. In order to determine whether the tumour-reactive T-lymphocytes should be subjected to one or more additional rounds of phase ii) one may look at the level of IFN-gamma produced, and/or the total number of tumour-reactive T-lymphocytes obtained and/or the expression of CD25. In the case the IFN-γ levels is 30 pg/ml culture medium or less, such as, e.g. 20 pg/ml culture medium or less, and/or the total number of T cells are unsatisfactory, additional rounds of phase ii) may be initiated beginning when the majority of T cells are CD25 negative (i.e. less than 5% of the T-lymphocytes population express CD25) and thereby susceptible to restimulation.

After harvest the tumour-reactive T-lymphocytes may be purified by any conventional means, such as, e.g. by using density gradient, such as, e.g., a Ficoll medium. A portion of the tumour-reactive T-lymphocytes may be stored by freezing in a suitable freezing medium after harvesting and purifying the tumour-reactive T-lymphocytes.

Administration

The tumour-reactive T-lymphocytes obtained by an improved expansion method are used herein for treating patients suffering from malignant melanoma.

The definition of an effective amount of tumour-reactive T-lymphocytes to be administered is depending on the specific type of lymphocytes, the ratio of memory to effector T-lymphocytes and on the severity of the disease. However, in average a minimum of at least 10 million, such as, e.g. at least 20 million, at least 30 million, at least 40 million, at least 50 million, at least 60 million, at least 70 million or at least 80 million tumour-reactive T-lymphocytes may be administered. The present inventors have not identified any upper limit with respect to the amount of tumour-reactive T-lymphocytes to be administered in a single dose.

In a preferred embodiment the tumour-reactive T-lymphocytes for administration comprises a combination of effector T-lymphocytes and memory T-lymphocytes. More specific the amount of tumour-reactive T-lymphocytes of the memory type may be from about 35% to about 90%, such as, e.g. from about 40% to about 90%, from about 50% to about 80% or from about 60% to about 70%, and a percentage of effector T-lymphocytes from about 10% to about 65%, such as, e.g., from about 20% to about 50% or from about 30% to about 40%.

The tumour-reactive T-lymphocytes may be formulated as a pharmaceutical composition suitable for parenteral administration to the patient such as, e.g., intravenously, intraarterially, intrathecally or intraperitonally administration.

When the tumour-reactive T-lymphocytes are administered parenterally, they may be formulated in an isotonic medium, i.e. in a medium having the same tonicity as blood, and comprising one or more substances preventing aggregation of the cells. A specific example of a suitable medium is a 0.9% NaCl solution comprising up to 3% human serum albumin such as, e.g. up to 2% human serum albumin or up to 1% human serum albumin. For intravenously administration the concentration of tumour-reactive T-lymphocytes in the composition to be administered normally lies within the range from about 0.5 million lymphocytes/ml medium to about 4 million lymphocytes/ml medium, such as, e.g., from about 0.5 million lymphocytes/ml medium to about 3 million lymphocytes/ml medium, from about 0.5 million lymphocytes/ml medium to about 2 million lymphocytes/ml medium or from about 1 million lymphocytes/ml medium to about 2 million lymphocytes/ml medium.

The composition comprising tumour-reactive T-lymphocytes may be administered as a single dose or multiple doses. It may be infused over 1 to 2 hours.

The treatment method may be performed once or repeated depending on the severity of the disease. Furthermore, the treatment may be reiterated upon recurrence of the disease.

The treatment according to the present invention may be supplemented with any other relevant treatment for malignant melanoma. Such supplemental treatment may be given before, at the same time or after the administration of the lymphocytes and it may be given at frequencies normally used for such treatments. A suitable example of supplemental treatment is chemotherapy and the like.

Kits

The invention further relates to kits for use in a method according to the invention, the kit comprising a medium for cultivation of T-lymphocytes. The medium may be any suitable serum-free medium, such as, e.g., AIMV, RPMI 1640, DMEM or MEM.

The kit may further comprise one or more substances for stimulating, activating and directing tumour-reactive T-lymphocytes. Examples of such substances may be tumour-derived antigen, substances having agonistic activity towards the IL-2 receptor, substances capable of up-regulating IL-12R on the T-lymphocytes, substances capable of antagonizing development of Th2 type T-lymphocytes and/or substances promoting the development of Th1 type T-lymphocytes.

More specific, such substances may be IL-2, interferon-alpha, anti-IL-4 antibody, anti-IL-5 antibody, anti-IL-10 antibody, IL-7, IL-12, IL-15 and/or IL-21.

The kit may also comprise a pharmaceutical composition suitable for intravenous administration. The pharmaceutical composition may be mixed with the population of tumour-reactive T-lymphocytes before administration.

The kit may also comprise one or more syringes and a lymph node locator. In one embodiment, the syringes are prefilled with a lymph node locator.

The kits may also comprise instructions for use, such as, e.g. instructions in the form of computer software.

FIGURE LEGENDS

Figure 1:
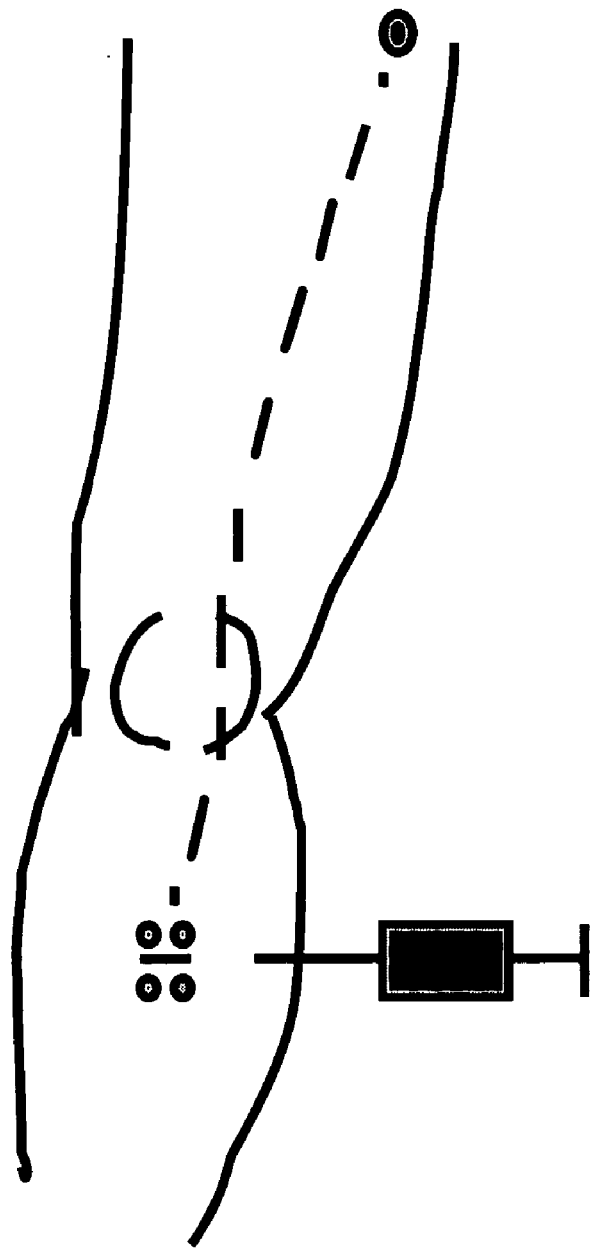
FIG. 1 shows the injection of isotope or patent blue around the malignant melanoma or around the scar after initial melanoma removal where after the lymphatic drainage of the tumour will stain and reveal the sentinel node.
Figure 2:
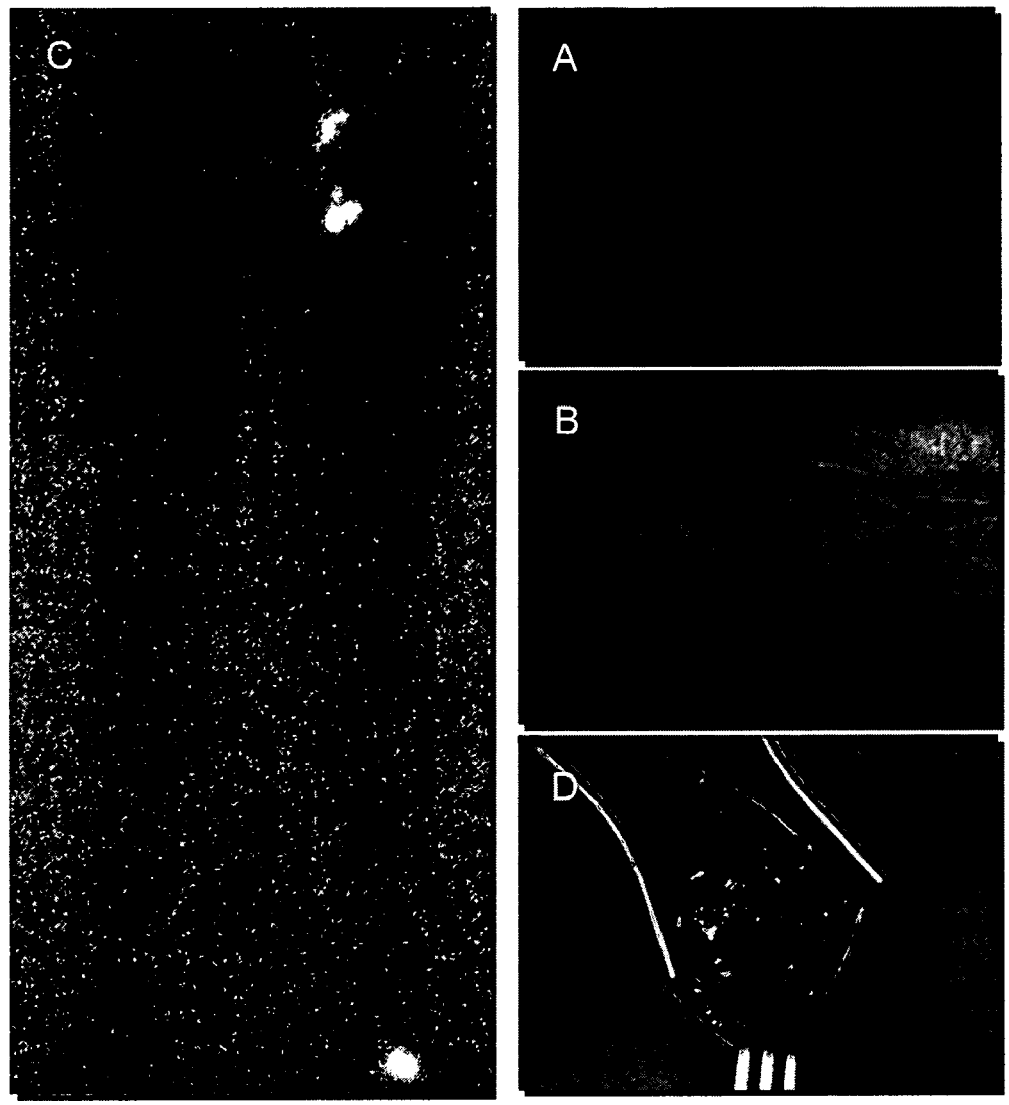
FIGS. 2A and 2B shows plantar malignant melanoma injected with radioactive tracer and patent blue. Sentinel node identified by scintigraphy (FIG. 2C) and by open surgery and dissection in area inguinalis (FIG. 2D).
Figure 3:
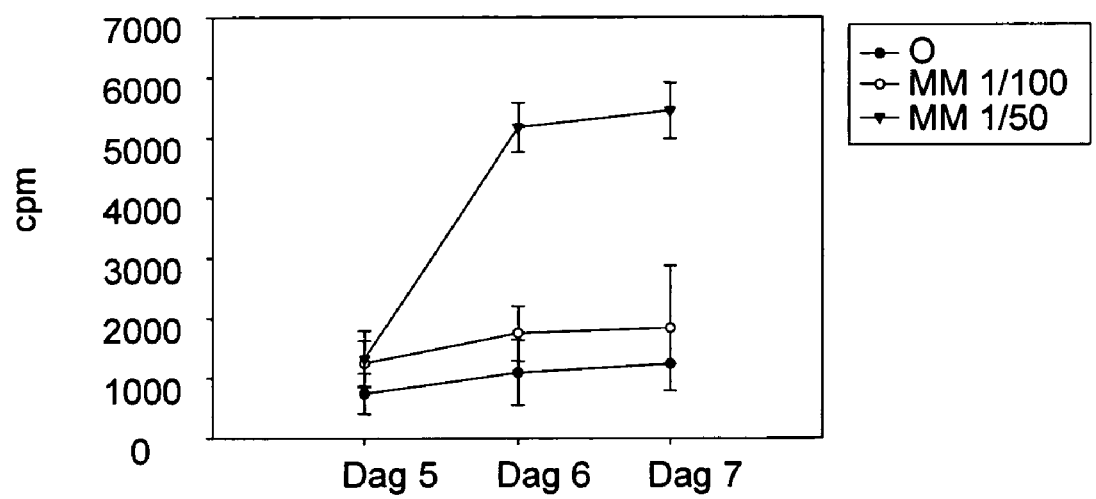
FIG. 3 shows a time course study of sentinel node acquired lymphocytes. '0' represents no addition of autologous tumour extract, 'MM 1/100' represents addition of a 1/100 dilution of tumour extract, and 'MM 1/50' represents addition of a 1/50 dilution of tumour extract. Proliferation, determined as cpm by scintillation counting, is seen at the highest concentration of autologous tumour extract.
Figure 4:
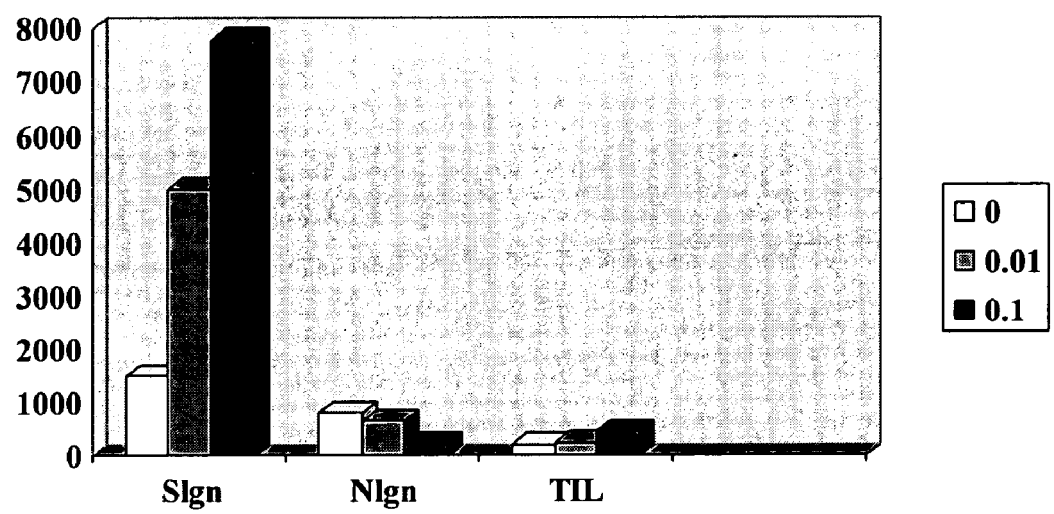

FIG. 4 illustrates that sentinel node acquired lymphocytes (Slgn) are proliferating dose dependently against autologous tumour extract, whereas no proliferation was seen among lymphocytes from a negative node (Nlgn) or from tumour infiltrating lymphocytes (TIL). The different bars illustrate proliferation in cpm, determined by scintillation counting, from 0, 1/100, and 1/10 dilution of tumour extract.

Figure 5:
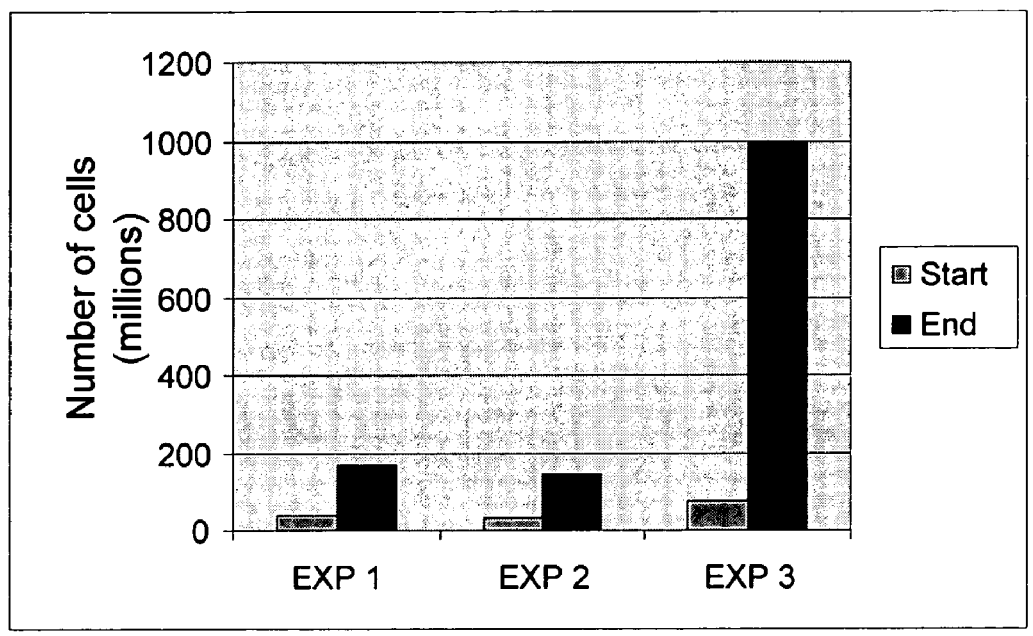

FIG. 5 shows that sentinel node acquired lymphocytes can be activated and expanded in the presence of autologous tumour extract and interleukin-2 as described above. Results are based on expansion of three different sentinel nodes from a patient with malignant melanoma. All experiments were carried out using the same expansion protocol, but generated various successes. An expansion of $1 \times 10^9$ cells was achieved in expansion 3.

Figure 6:
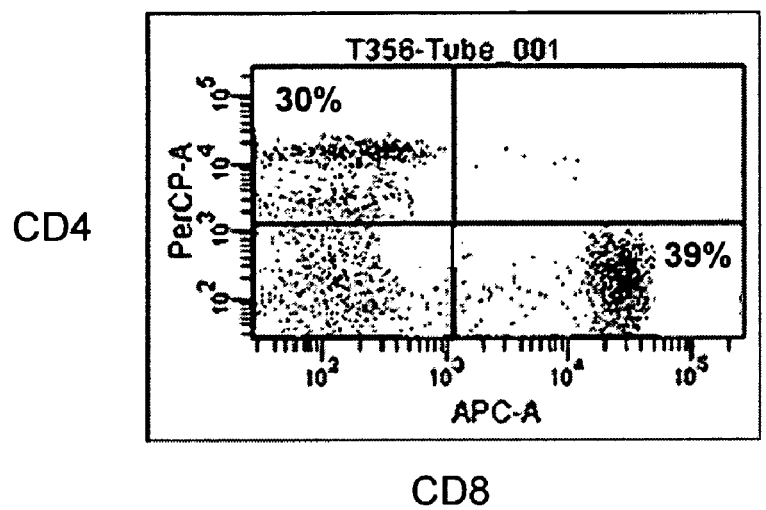
Figure 6:
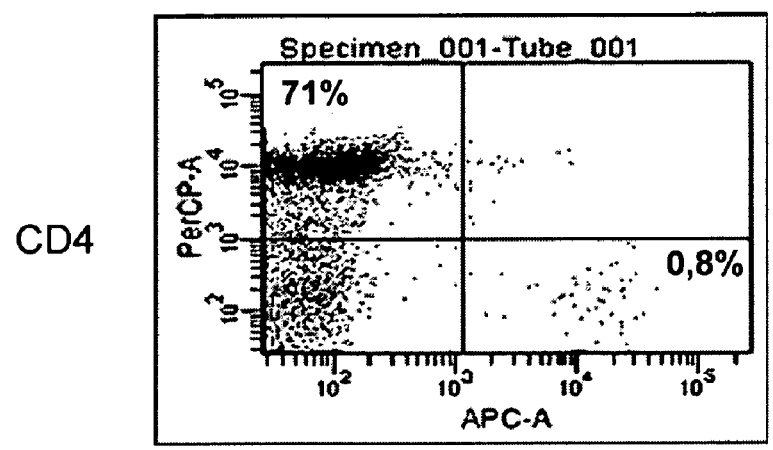

FIG. 6 shows the cellular expression of CD8 and CD4 T helper cell markers as investigated by flow cytometry. At the end of the expansion after approximately 30 days the majority of cells express the CD4 T helper cell marker.

Figure 7:
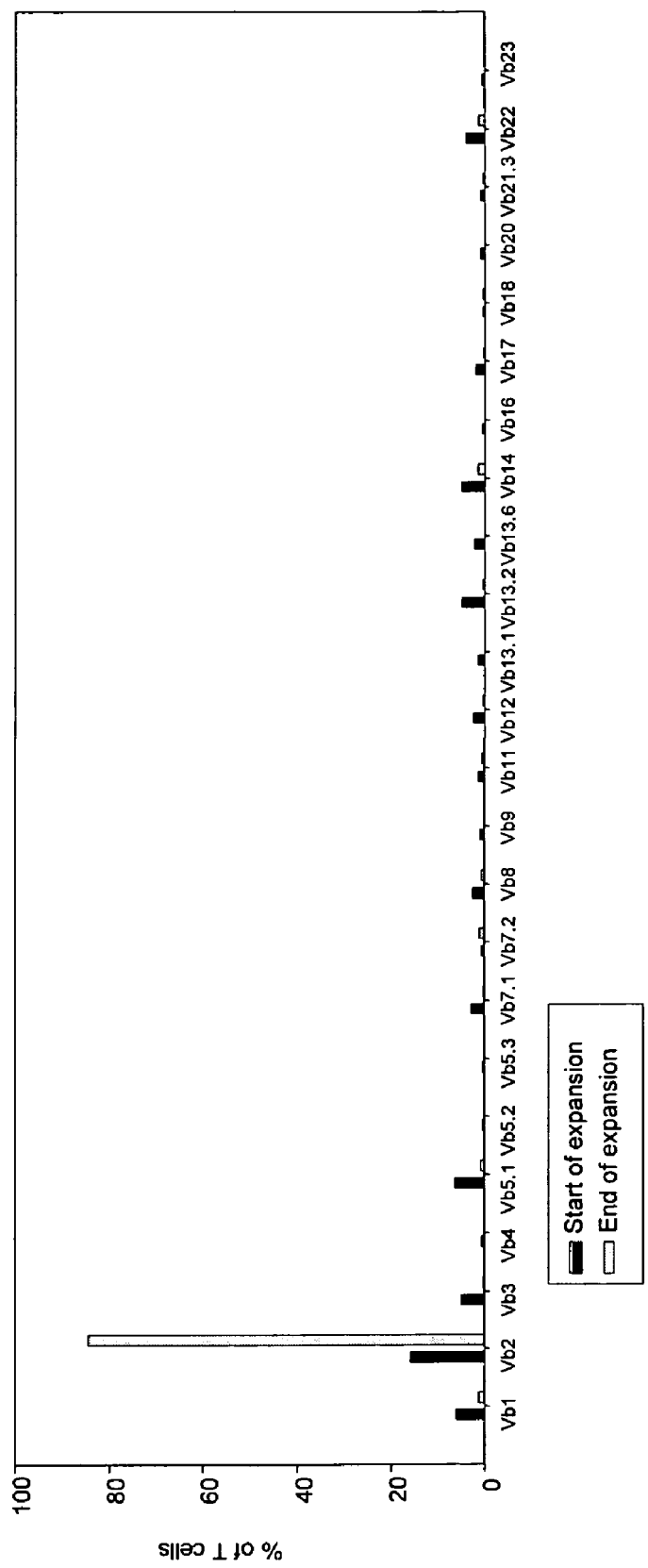

FIG. 7 shows the Vβ repertoire before and after expansion as investigated by flow cytometry. The majority of cells at the end of the expansion belong to the Vβ2 family indicating clonal expansion of tumour reactive T cells.

Figure 8:
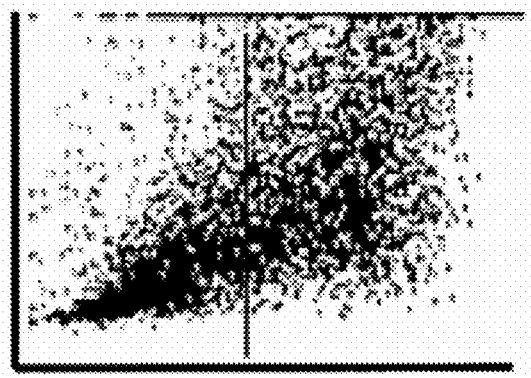
Figure 8:
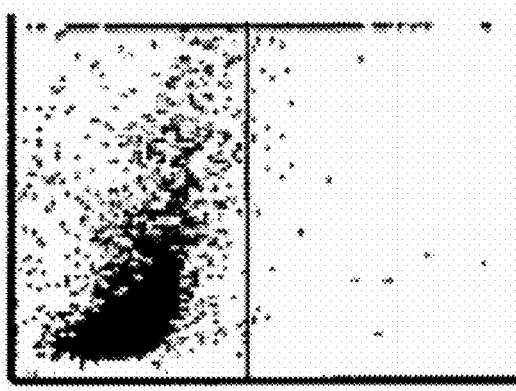

FIG. 8 shows the presence of metastatic malignant melanoma cells in sentinel lymph nodes with metastasis as investigated by flow cytometry using antibodies against HMB-45. SSC indicates side scatter, which is an indication of the granularity of cells.

Figure 9:
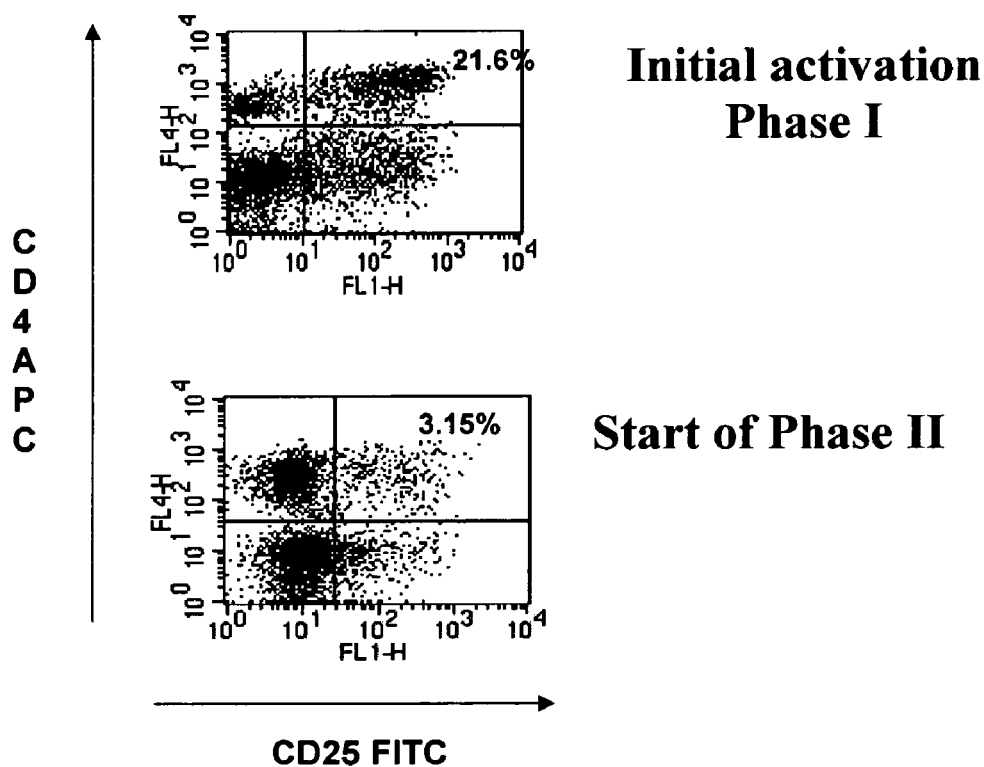

FIG. 9 shows that initially sentinel node lymphocytes are activated with tumor antigen and low dose IL-2 resulting in activation and expression of the activation marker CD25 (Top panel). The end of phase I activation phase is defined by the decreased number of CD4$^+$ T cells expressing CD25 (Bottom panel). When less than 5% of the CD4$^+$ T cells express CD25 phase II is initiated with restimulation with antigen.

Figure 10:
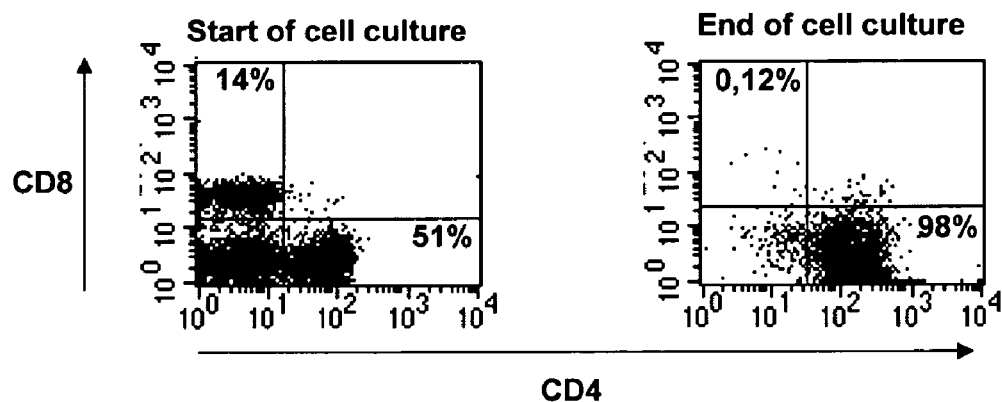

FIG. 10 illustrates that Phase I and Phase II activation results in expansion and enrichment of CD4$^+$ T helper cells.

Figure 11:
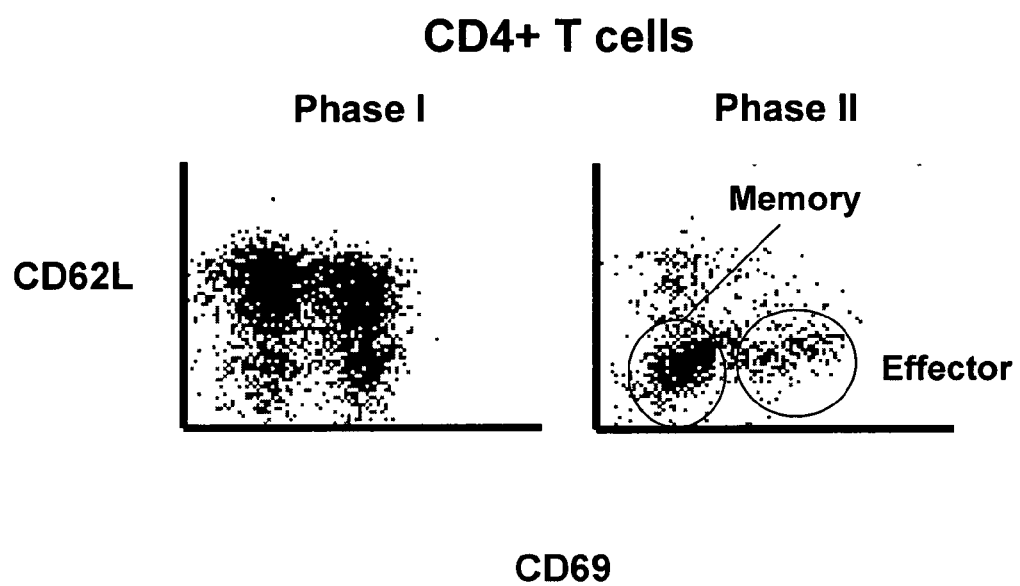

FIG. 11 illustrates that in Phase I the majority of cells are naive CD62L+ cells or activated CD69+CD62L+ cells. After Phase II the majority of the cells are CD62L– and are composed of memory and effector CD4+ T helper cells. CD62L– T cells are not expressing the preferred lymph node homing molecule, thus they are seeking inflammatory areas in non-lymphatic organs.

Figure 12:
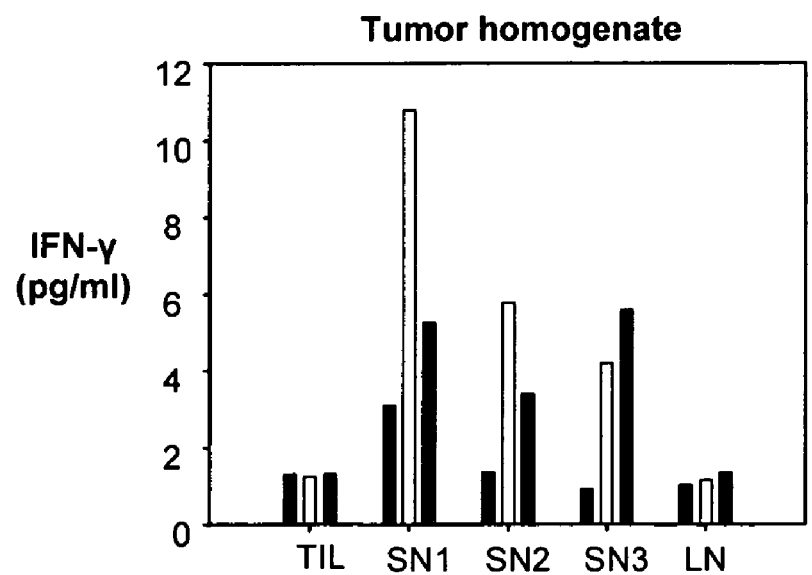

FIG. 12 shows primary cells stimulated in Phase I from the tumour (Tumour infiltrating lymphocytes), sentinel nodes (SN) and an irrelevant lymph node (LN) results in no little IFN-gamma production.

Figure 13:
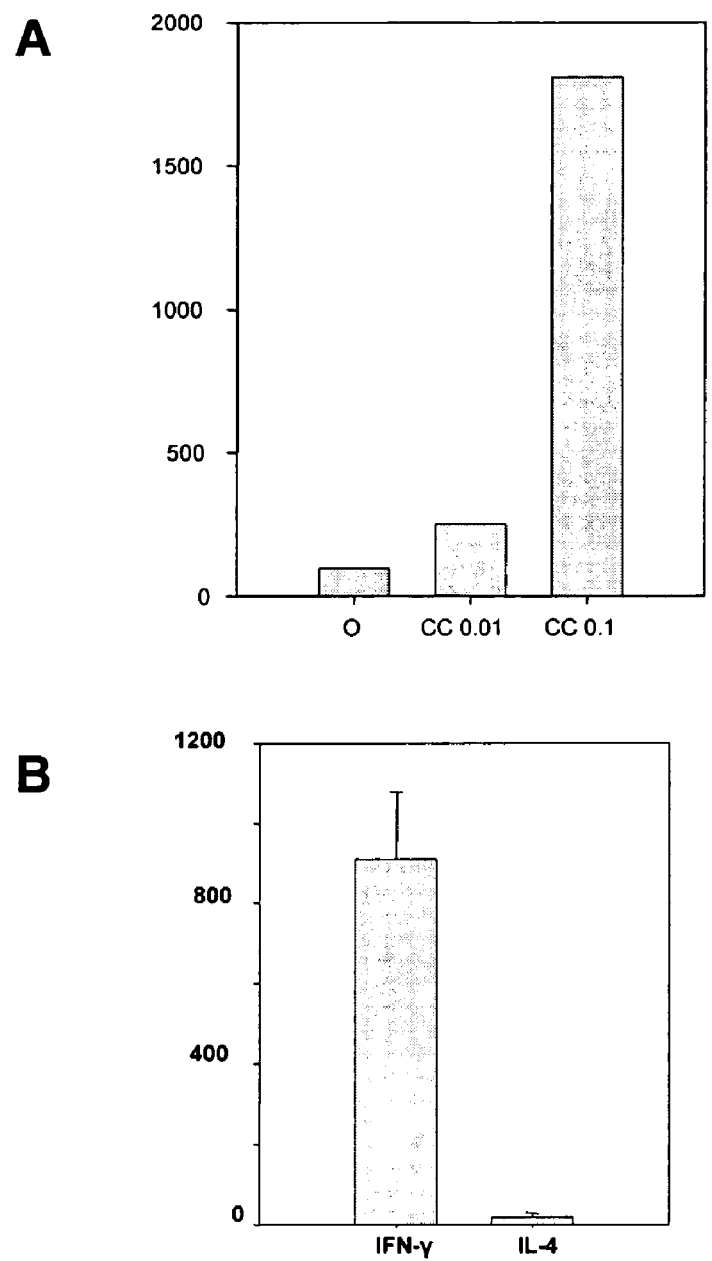

FIG. 13 illustrates that after expansion after phase ii) there is a dose dependent increase in antigen dependent IFN-gamma production.

Figure 14:
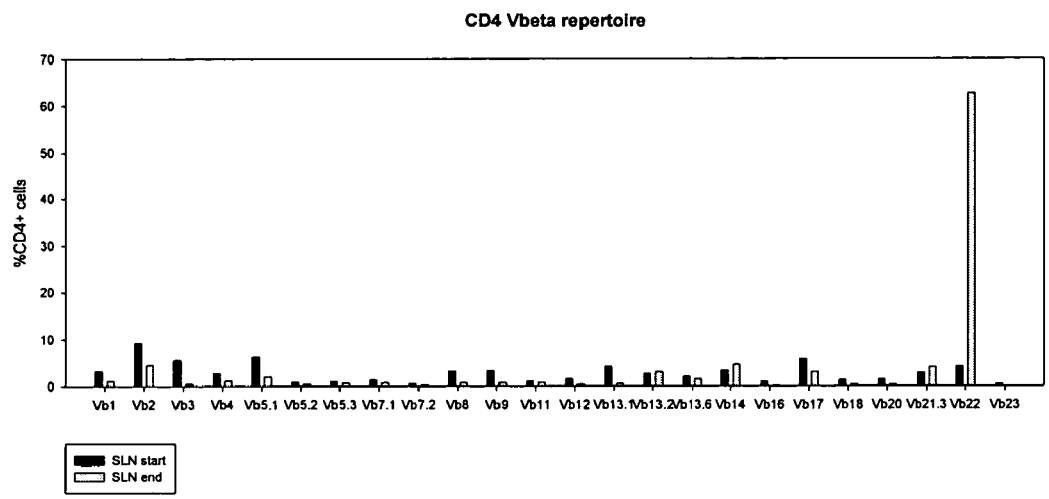

FIG. 14 illustrates that the expansion and activation protocol promotes the expansion of antigen specific T cell clones as investigated by the selective enrichment of TCR V beta expression.

The following examples tend to illustrate the invention without limiting it in any way.

EXAMPLES

Example 1

Acquirement and Expansion of Tumour-Reactive T-lymphocytes from Patient with Malignant Melanoma Materials and Methods Patients Patients with malignant melanoma were included in the study. The study was approved by the local ethical committee and informed consent was given by the patients.

Identification of Sentinel Nodes

One ml Patent blue dye (Guerbet, Paris) in addition to 0.4 ml of the isotope 40 MBq$^{99mTc}$-Albu-Res was injected superficially around the primary tumour. Sentinel lymph nodes were identified by hand held γ-counter.

Preparation of Specimens

The sentinel and non-sentinel nodes were cut in half. Slices were cut from the central and the peripheral part of the nodes for flow cytometry, proliferation analysis and expansion. The rest of the node underwent routine histopathological examination. One piece of the primary tumour (including part of the invasive margin) was removed for flow cytometry analyses and as an antigen source.

Flow Cytometry Analyses

PBL, lymph node cells and tumour cell suspensions at $1 \times 10^6$ cells/sample were subjected to investigation using flow cytometry (FACS). Cells were washed in PBS containing 2% FCS and 0.05% NaN$_3$ and stained with fluorophore conjugated antibodies against the cell surface molecules CD4 PE, CD8 PerCp (Becton Dickinson) and the very early activation marker CD69 FITC (Pharmingen). The Vβ-TCR repertoire was examined using the Beta mark kit (Beckman Coulter), $5 \times 10^5$ cells/tube being stained in 10 μl of the 8 different vials containing mixtures of FITC, PE and dual-colour FITC-PE conjugated TCR Vβ antibodies. In addition, direct conjugated antibodies CD8 PerCP and CD4 APC were added to each tube. After staining, cells were investigated using a FACS-Calibur (Becton Dickinson) and data were analyzed using the Cellquest computer software (Becton Dickinson).

Immunological Evaluation

Single cell suspensions from lymph nodes and tumours were obtained by gentle pressure using a loose fit glass homogenizer. Peripheral blood leukocytes (PBL) were purified by ficoll-paque (Pharmacia, Amersham). Cells were resuspended and washed twice in RPMI 1640 (Life technologies) containing 2.5% fetal calf serum (FCS) (Life technologies). Finally, cells were resuspended in RPMI 1640 proliferation media containing 10% human AB serum (Sigma), 1% penicillin-streptomycin (Sigma) and 1% glutamine (Sigma). Tumour samples were homogenized using a Ultra-turrax in 5 volumes (w/v) of 2×PBS followed by 5 minutes denaturation at 97° C. Tumour homogenates were diluted to 1:10 and 1:100 in complete proliferation media. Purified PBL and lymph node cells were used at $3 \times 10^5$ cells/well in time course proliferation assays against diluted tumour homogenate, Con A 10 μg/ml (Sigma) or tyrosinase peptide 100 μg/ml (Sigma) in triplicate. Proliferation was measured by adding 1 μCi of $^3$H-Thymidine/well (Amersham) 18 hours prior to harvesting. Samples were subjected to scintillation counting.

Example 2

General Method for Expansion of Tumour-Reactive T-lymphocytes

Cell Culture

Phase I, Initial Activation

The node material was kept on ice and immediately taken care of using AIM V® Media (Invitrogen) at all times. Single cell suspensions of sentinel or metinel node lymphocytes was obtained through gentle homogenisation in a loose fit glass homogenisator, and following homogenisation cells were washed twice in medium. The metinel node lymphocytes were put in cell culture flasks at 4 million cells/ml and interleukin-2 (IL-2) (Proleukin®, Chiron) was added to a concentration of 240 IU/ml medium.

Autologous metastasis extract was prepared by homogenisation with an Ultra Turrax in 5 volumes (w/v) 2×PBS followed by denaturation for 5 minutes at 97° C. Three to four days after initiation of the cell culture autologous tumour extract was added at a concentration of $1/100$. For long-term culture the cells were kept in a cell incubator at 37° C. and 5% CO2 and 240 IU IL-2/ml media added every 3-4 days.

Phase II, Activation and Expansion

After 18-22 days the cell cultures were monitored for the expression of CD25. When the number of CD25 expressing cells was diminished below 5% the cells were restimulated in Phase II (FIG. 9) by the addition of autologus metastasis extract at a concentration of $1/100$. For efficient antigen presentation autologous PBMC were collected using Ficoll-Paque PLUS (Amersham Biosciences, GE Healthcare), radiated with 2500 rad and added to the cell cultures. Three days after restimulation interferon-α (Introna) in conc. 100-500 IU/ml and anti IL-4 antibody was added to a concentration of 2 µg/ml. After 5 to 8 days IL-12 (4 ng/ml) was added to the expansion in order to promote induction of IFN-γ producing Th1 cells.

The day before transfusion to the patient the cell cultures were subject to purification using a Ficoll-Paque PLUS (Amersham Biosciences, GE Healthcare) in order to retrieve the viable cells in the culture. On the day of transfusion the cells were washed twice in Saline solution (Natriumklorid Baxter Viaflo 9 mg/ml, Baxter) and then transferred to a transfer bag containing 100-200 ml of saline solution and 1% Human Serum Albumin (Baxter). Investigations for microbial presence were performed prior to transfusion. Infusions of the cells were performed during 1-2 hours under professional medical supervision.

Immunological Evaluation

Further immunological evaluation was performed using tritium labeled thymidine incorporation proliferation assays. An aliquot of metinel node lymphocytes was set aside for this purpose, a single cell suspension of non-metinel node lymphocytes was obtained by gentle pressure in a loose fit glass homogenisator and peripheral blood leukocytes were purified by Ficoll-Paque PLUS (Amersham Biosciences, GE Healthcare).

Cells were resuspended and washed twice in RPMI 1640 (Life technologies) containing 2.5% fetal calf serum (FCS) (Life technologies). Finally, cells were resuspended in RPMI 1640 proliferation media containing 10% human AB serum (Sigma), 1% penicillin-streptomycin (Sigma) and 1% glutamine (Sigma). Lymph node cells and purified PBL were used at $3 \times 10^5$ cells/well in a 96-well plate and stimulated with metastasis homogenate diluted $1/100$, $1/10$ or Con A 10 µg/ml (Sigma) in triplicates. Proliferation was measured on day 5, 6 and 7 by adding 1 µCi of $^3$H-Thymidine/well (Amersham) 18 hours prior to harvesting. Samples were subjected to scintillation counting.

At the start of cell culture, stimulations of lymph node cells and PBL, for the measurement of IFN-γ secretion, were performed in 96-well plates with $3 \times 10^5$ cells/well in triplicate with tumour homogenate diluted $1/10$ and $1/100$, or Con A 10 µg/ml (Sigma). The amount of secreted IFN-γ was measured with ELISA (Human IFN-γ Duoset, R&D Systems) on culture supernatants in pooled samples of the triplicates (FIG. 12). At the end of cell cultures samples of the supernatant was removed and IFN-γ and IL-4 secretion measured in triplicates with ELISA (Human IFN-Duoset and Human IL-4 Duoset, R&D Systems) (FIGS. 13A and 13B).

Flow Cytometry Analyses

Characterization of cells was performed using flow cytometry initially on cells from the metinel node, non-metinel node, PBMC and from the metastasis. From the metinel node acquired lymphocytes in culture samples were taken every two to three weeks for flow cytometry analyses. Cells were incubated for 30 minutes in PBS supplemented with 2% FCS and 0.05% NaN$_3$ (FACS buffer) with antibodies against markers for immune cell subpopulations and for lymphocyte activation (FIGS. 9, 10 and 11). Antibodies conjugated with Fluorescein isothiocyanate (FITC) against the following markers were used: CD69, HLA-DR, CD45RA, CD25, conjugated with phycoerythrin (PE): CD62L, CD19, CD45RO, CD56, conjugated with Peridinin-Chlorophyll-Protein (PerCP): CD8, CD3, conjugated with allophycocyanin (APC): CD4, CD14, CD8.

The Vβ-repertoire was examined using the Beta mark kit (Beckman Coulter), $5 \times 10^5$ cells/tube was stained in 10 µl of the 8 different vials containing mixtures of FITC, PE and dual-colour FITC-PE conjugated TCR Vβ antibodies and with the addition of CD8 PerCP and CD4 APC to each tube (FIG. 14).

Specific Embodiments

1. A method for treating a patient suffering from malignant melanoma, the method comprising
    i) identifying in a patient one or more sentinel and/or metinel lymph nodes draining a malignant melanoma or a metastasis there from;
    ii) resecting the one or more nodes and, optionally all or part of the tumour or metastasis;
    iii) isolating tumour-reactive T-lymphocytes from said lymph nodes:
    iv) in vitro expanding said tumour-reactive T-lymphocytes, wherein the in vitro expansion comprises
        i) a first phase of stimulating tumour-reactive CD4+ helper and/or CD8+ T-lymphocytes with tumour-derived antigen together with at least one substance having agonistic activity towards the IL-2 receptor to promote survival of tumour-reactive CD4+ helper and/or CD8+ T-lymphocytes, and
        ii) a second phase of activating and promoting growth of tumour-reactive CD4+ helper and/or CD8+ T-lymphocytes, wherein the second phase ii) is initiated when the CD25 cell surface marker (or IL-2R marker) is down-regulated on T-lymphocytes;
    v) administering the thus obtained tumour-reactive T-lymphocytes to the patient;
wherein the T-lymphocytes are CD4+ helper and/or CD8+ T-lymphocytes.

2. A method according to embodiment 1 or 2, wherein the one or more lymph nodes are identified in step i) by injecting one or more lymph node locators into the patient.
3. A method according to any of the preceding embodiments, wherein the one or more lymph node locators are affinity based.
4. A method according to any of the preceding embodiments, wherein the one or more lymph node locators are non-affinity based.
5. A method according to any of the preceding embodiments wherein one or more lymph node locators are injected into, above, around, adjacent and/or under the tumour or metastasis.
6. A method according to any of the preceding embodiments, wherein the one or more lymph node locators are injected by a single injection.
7. A method according to any of embodiments 1-5, wherein the one or more lymph node locators are injected by multiple injections.
8. A method according to any of the preceding embodiments, wherein the one or more lymph node locators are injected by a non-surgical procedure.
9. A method according to any of embodiments 1-79, wherein the one or more lymph node locators are injected as part of a surgical procedure.
10. A method according to any of the preceding embodiments, wherein all or part of the tumour or metastasis is removed from the patient.
11. A method according to embodiment 10, wherein the down-regulation is defined as that 5% or less of the T-lymphocyte population expresses CD25.
12. A method according to embodiment 10 or 11, wherein the T-lymphocytes are present in a culture medium.
13. A method according to embodiment 12, wherein the culture medium is a serum-free medium, such as, e.g. AIMV medium.
14. A method according to any of the preceding embodiments, wherein the first phase i) is initiated by adding the at least one substance having agonistic activity towards the IL-2 receptor.
15. A method according to embodiment 14, wherein the substance having agonistic activity towards the IL-2 receptor is IL-2.
16. A method according to embodiment 15, wherein IL-2 is added in a low dose, such as, e.g., from about 100 IU/ml culture medium to about 700 IU/ml culture medium, from about 100 IU/ml culture medium to about 600 IU/ml culture medium, from about 100 IU/ml culture medium to about 500 IU/ml culture medium, from about 100 IU/ml culture medium to about 400 IU/ml culture medium, from about 100 IU/ml culture medium to about 300 IU/ml culture medium and from about 100 IU/ml culture medium to about 200 IU/ml culture medium.
17. A method according to any of the preceding embodiments, wherein a further amount of the at least one substance having agonistic activity towards the IL-2 receptor is added regularly throughout phase i), such as, e.g., every $2^{nd}$, $3^{rd}$ or $4^{th}$ day of phase i).
18. A method according to embodiment 17, wherein the substance having agonistic activity towards the IL-2 receptor is IL-2.
19. A method according to embodiment 18, wherein the concentration of IL-2 added is from about 100 IU/ml culture medium to about 700 IU/ml culture medium, from about 100 IU/ml culture medium to about 600 IU/ml culture medium, from about 100 IU/ml culture medium to about 500 IU/ml culture medium, from about 100 IU/ml culture medium to about 400 IU/ml culture medium, from about 100 IU/ml culture medium to about 300 IU/ml culture medium and from about 100 IU/ml culture medium to about 200 IU/ml culture medium.
20. A method according to any of the preceding embodiments, wherein the tumour-derived antigen is added from day 2 to and including day 5 of the first phase i), such as, e.g., on day 2, on day 3, on day 4 or on day 5.
21. A method according to any of embodiments 1 or 10-19, wherein the tumour-derived antigen is added essentially at the same time as when phase i) is initiated or at the most up to 3 days thereafter.
22. A method according to any of the preceding embodiments, wherein the tumour-derived antigen is a denatured homogenate of a tumour.
23. A method according to any of the preceding embodiments, wherein the tumour-derived antigen is a protein, polypeptide or peptide.
24. A method according to any of the preceding embodiments, wherein the second phase ii) is initiated from day 17 to and including day 23 of the first phase i), such as, e.g. on day 17, on day 18, on day 19, on day 20 on day 21, on day 22 or on day 23.
25. A method according to any of the preceding embodiments, wherein the second phase is initiated by the addition of tumour-derived antigen to the T-lymphocytes for activating tumour-reactive CD25-negative T-lymphocytes.
26. A method according to embodiment 25, wherein the tumour-derived antigen is a denatured homogenate of a tumour.
27. A method according to embodiment 25, wherein the tumour-derived antigen is a tumour protein, polypeptide or peptide.
28. A method according to any of embodiments 25-27, which further comprises addition to the T-lymphocytes of antigen presenting cells together with the tumour-derived antigen.
29. A method according to embodiment 19, wherein the antigen presenting cells are irradiated peripheral blood leucocytes containing antigen-presenting B-cells and/or monocytes.
30. A method according to any of the preceding embodiments, wherein the second phase ii) comprises adding at least one substance capable of up-regulating IL-12R on the T-lymphocytes.
31. A method according to embodiment 30, wherein the substance(s) capable of up-regulating IL-12R on the T-lymphocytes is substance(s) having agonistic activity towards an interferon receptor.
32. A method according to embodiment 31, wherein the substance(s) having agonistic activity towards an interferon receptor is an interferon.
33. A method according to embodiment 32, wherein the substance(s) having agonistic activity towards an interferon receptor is interferon-α.
34. A method according to any of embodiments 30-33, wherein the substance(s) capable of up-regulating IL-12R on the T-lymphocytes, such as, e.g. a substance having agonistic activity towards an interferon receptor, is added when the level of IL-12 is at least 1 fold, such as, e.g., at least 2, at least 3 fold, at least 4 fold, or at least 5 fold increased as compared to the level of IL-12 on day 1 of phase ii).
35. A method according to any of embodiments 30-34, wherein the substance capable of up-regulating IL-12R on the T-lymphocytes, such as, e.g. a substance having agonistic activity towards an interferon receptor is added from 35. ...day 2 to and including day 4 after initiating the second phase ii), such as, e.g. on day 2, on day 3 or on day 4.
36. A method according to any of the preceding embodiments, wherein the second phase ii) comprises adding one or more substances capable of antagonizing development of Th2 type T-lymphocytes.
37. A method according to embodiment 36, wherein the one or more substances capable of antagonizing development of Th2 type T-lymphocytes are one or more substances capable of neutralizing IL-4, IL-5, IL-10, and/or TGF-beta.
38. A method according to embodiment 37, wherein the one or more substances capable of neutralizing IL-4, IL-5, IL-10, and/or TGF-beta are anti IL-4 antibody, anti IL-5 antibody and/or anti IL-10 antibody.
39. A method according to any of embodiments 36-38, wherein the one or more substances capable of antagonizing development of Th2 type T-lymphocytes, such as, e.g., one or more substances capable of neutralizing IL-4, IL-5, IL-10, and/or TGF-beta is added on day 1 of the second phase ii).
40. A method according to any of embodiments 36-38, wherein the one or more substances capable of antagonizing development of Th2 type T-lymphocytes, such as, e.g., one or more substance capable of neutralizing IL-4, IL-5, IL-10, and/or TGF-beta is added in a subsequent step after addition of the substance capable of up-regulating IL-12R on the T-lymphocytes.
41. A method according to embodiment 40, wherein the one or more substances capable of antagonizing development of Th2 type T-lymphocytes, such as, e.g., one or more substance capable of neutralizing IL-4, IL-5, IL-10, and/or TGF-beta is added one day after addition of the substance capable of up-regulating IL-12R on the T-lymphocytes.
42. A method according to any of the preceding embodiments, wherein a further amount of the one or more substance capable of antagonizing development of Th2 type T-lymphocytes, such as, e.g., one or more substance capable of neutralizing IL-4, IL-5, IL-10 and/or TGF-beta is added regularly throughout phase ii).
43. A method according to embodiment 42, wherein a further amount of the one or more substance capable of antagonizing development of Th2 type T-lymphocytes, such as, e.g., one or more substance capable of neutralizing IL-4, IL-5, IL-10 and/or TGF-beta is added every $2^{nd}$, $3^{rd}$ or $4^{th}$ day of phase ii).
44. A method according to any of the preceding embodiments, wherein a further amount of a substance having agonistic activity towards the IL-2 receptor is added regularly throughout phase ii).
45. A method according to embodiment 44, wherein the substance having agonistic activity towards the IL-2 receptor is added every $2^{nd}$, $3^{rd}$ or $4^{th}$ day of phase ii), such as, e.g., every $3^{rd}$ day.
46. A method according to embodiment 44 or 45, wherein the substance having agonistic activity towards the IL-2 receptor is IL-2.
47. A method according to any of the preceding embodiments, wherein the second phase ii) comprises adding one or more substances promoting the development of Th1 type T-lymphocytes.
4. A method according to embodiment 47, wherein the one or more substances promoting the development of Th1 type T-lymphocytes is substances having agonistic activity towards the IL-7, IL-12, IL-15 and/or IL-21 receptor.
49. A method according to embodiment 48, wherein the one or more substances is selected from IL-7, IL-12, IL-15 and IL-21.
50. A method according to any of embodiments 47-49, wherein one or more substances promoting the development of Th1 type T-lymphocytes, such as, e.g., substances having agonistic activity towards the IL-7, IL-12, IL-15 and/or IL-21 receptor is added when the level of IFN-gamma is increased as compared to the level of IFN-gamma on initiation of second phase ii).
51. A method according to embodiment 50, wherein the increased level of IFN-gamma is determined as at least a 1 fold increase in IFN-gamma level, such as, e.g., at least a 2 fold, at least a 3 fold, at least a 4 fold increase as compared to the level of IFN-gamma on initiation of the second phase ii).
52. A method according to any of embodiments 47-51, wherein the one or more substances promoting the development of Th1 type T-lymphocytes, such as, e.g., substances having agonistic activity towards the IL-12, IL-15 and/or IL-21 receptor is added when CD25 and/or CD69 are down-regulated.
53. A method according to any of embodiments 47-52, wherein the concentration of each of the one or more substances promoting the development of Th1 type T-lymphocytes, such as, e.g., substances having agonistic activity towards the IL-7, IL-12, IL-15 and/or IL-21 receptor added is from about 150 IU/ml culture medium to about 300 IU/ml culture medium, such as, e.g. 250 IU/ml culture medium.
54. A method according to any of embodiment 47-53, wherein the one or more substances promoting the development of Th1 type T-lymphocytes, such as, e.g., substances having agonistic activity towards the IL-12, IL-15 and/or IL-21 receptor is added from day 5 to and including day 8 after initiating the second phase ii), such as, on day 5, day 6, day 7 or day 8.
55. A method according to any of the preceding embodiment for the preparation of CD4+ helper T lymphocytes.
56. A method according to any of the preceding embodiments for the preparation of effector T-lymphocytes.
57. A method according to any of the preceding embodiments for the preparation of memory T-lymphocytes.
58. A method according to any of the preceding embodiments for the preparation of Th1 type T-lymphocytes.
59. A method according to any of the preceding embodiments, which further comprises monitoring the expression of cell surface markers, such as, e.g., CD25 and/or CD69 on the T-lymphocytes continuously during the first phase i) and second phase ii).
60. A method according to embodiment 59, wherein the T-lymphocytes are harvested when CD25 on T-lymphocytes in the second phase ii) is down-regulated.
61. A method according to embodiment 60, wherein the T-lymphocytes are subjected to at least one additional round of phase ii), when CD25 on T-lymphocytes is down-regulated.
62. A method according to embodiment 60 or 61, wherein the down-regulation is defined as that 5% or less of the CD4 positive T-lymphocyte population expresses CD25.
63. A method according to any of the preceding embodiments, wherein the tumour-reactive T-lymphocytes are harvested from day 10 to and including day 14 after initiating the second phase ii).
64. A method according to embodiment 63, wherein the tumour-reactive T-lymphocytes are purified after harvest.
65. A method according to any of the preceding embodiments further comprising a step of freezing the tumour-reactive T-lymphocytes obtained in the second phase ii).

66. A method according to any of the preceding embodiments, wherein the T-lymphocytes are derived from lymph nodes draining a primary tumour and/or a metastasis, or they are derived from blood.
67. A method according to any of the preceding embodiments, wherein the tumour-reactive T-lymphocytes in step iv) are administered intravenously, intraarterially or intrathecally, intraperitonally.
68. A method according to any of the preceding embodiments, wherein the amount of tumour-reactive T-lymphocytes administered is at least 10 million, such as, e.g. at least 20 million, at least 30 million, at least 40 million, at least 50 million, at least 60 million, at least 70 million or at least 80 million.
69. A method according to any the preceding embodiments, wherein the tumour-reactive T-lymphocytes administered are a combination of effector T-lymphocytes and memory T-lymphocytes.
70. A method according to embodiment 69, wherein the percentage of effector T-lymphocytes is from about 10% to about 65%, such as, e.g., from about 20% to about 50% or from about 30% to about 40%.
71. A method according to any of the preceding embodiments, wherein the tumour-reactive T-lymphocytes are autologous.
72. A method according to any of the preceding embodiments, wherein the tumour-reactive T-lymphocytes are non-autologous.
73. A tumour-reactive T-lymphocyte prepared according to the method defined in any of embodiments 1-72.
74. A tumour-reactive T-lymphocyte according to embodiment 73, which is a CD4+ T-lymphocyte.
75. A tumour-reactive T-lymphocyte according to embodiment 73 or 74, which is an effector T-lymphocyte.
76. A tumour-reactive T-lymphocyte according to any of embodiments 73-75, which is a memory T-lymphocyte.
77. A tumour-reactive T-lymphocyte according to any of embodiments 73-76, which is a Th1 type T-lymphocyte.
78. Use of tumour-reactive T-lymphocytes according to any of embodiments 73-7, for the preparation of a medicament for the treatment of disseminated cancer.
79. Kit for use in a method according to any of embodiments 1-72, the kit comprising a media for cultivation of T-lymphocytes.
80. Kit according to embodiment 79 further comprising one or more substances for stimulating, activating and directing tumour-reactive T-lymphocytes.
81. Kit according to embodiment 79 or 80, wherein the media a serum free medium, such as, e.g. AIMV, RPMI 1640, DMEM or MEM.
82. Kit according to any of embodiments 79-81, wherein the one or more substances for stimulating, activating an directing tumour-reactive T-lymphocytes are selected from tumour-derived antigen, substances having agonistic activity towards the IL-2 receptor, substances capable of up-regulating IL-12R on the T-lymphocytes, substances capable of antagonizing development of Th2 type T-lymphocytes and substances promoting the development of Th1 type T-lymphocytes.
83. Kit according to any of embodiments 79-82, wherein the one or more substances for stimulating, activating and directing tumour-reactive T-lymphocytes are selected from the group comprising IL-2, interferon-alpha, anti-IL-4 antibody, anti-IL-5 antibody, anti-IL-10 antibody, IL-7, IL-12, IL-15 and IL-21.
84. Kit according to any of embodiments 79-83, comprising a pharmaceutical composition suitable for intravenous administration.
85. A kit for detection of metinel lymph nodes, the kit comprising a syringe and a lymph node locator.
86. A kit for detection of metinel lymph nodes, the kit comprising a syringe prefilled with a lymph node locator.
87. Kit according to any of embodiments 79-86 further comprising instructions for use.
88. Kit according to embodiment 87, wherein the instructions are in the form of computer software.

The invention claimed is:

1. A method for treating a patient suffering from malignant melanoma, the method comprising:
   i) identifying in a patient one or more sentinel or metinel lymph nodes draining a malignant melanoma tumour or a metastasis from a malignant melanoma tumour;
   ii) resecting the one or more lymph nodes and, optionally all or part of the tumour or metastasis;
   iii) isolating tumour-reactive T-lymphocytes from said lymph nodes;
   iv) in vitro expanding said tumour-reactive T-lymphocytes, wherein the in vitro expansion comprises
      a) a first phase of stimulating tumour-reactive CD4+ helper or CD8+ T-lymphocytes with tumour-derived antigen together with at least one substance having agonistic activity towards the IL-2 receptor to promote survival of tumour-reactive CD4+ helper or CD8+ T-lymphocytes, and
      b) a second phase of activating and promoting growth of tumour-reactive CD4+ helper or CD8+ T-lymphocytes, wherein the second phase is initiated when a CD25 cell surface marker or IL-2R marker is down-regulated on T-lymphocytes; and
   v) administering the thus obtained tumour-reactive T-lymphocytes to the patient;
wherein the T-lymphocytes are CD4+ helper or CD8+ T-lymphocytes.

2. A method according to claim 1, wherein the down-regulation is defined as that 5% or less of the T-lymphocyte population expresses CD25.

3. A method according to either of claim 1 or 2, wherein the first phase is initiated by adding the at least one substance having agonistic activity towards the IL-2 receptor.

4. A method according to claim 1, wherein the tumour-derived antigen is a denatured homogenate of a tumour.

5. A method according to either of claim 1 or 4, wherein the second phase is initiated by the addition of malignant melanoma-derived antigen to the T-lymphocytes for activating tumour-reactive CD25-negative T-lymphocytes.

6. A method according to claim 5, wherein the malignant melanoma-derived antigen is a denatured homogenate of a tumour.

7. A method according to claim 1, which further comprises addition of antigen presenting cells to the T-lymphocytes together with the tumour-derived antigen.

8. A method according to claim 7, wherein the antigen presenting cells are irradiated peripheral blood leucocytes containing antigen-presenting B-cells and/or monocytes.

9. A method according to claim 1, wherein the second phase comprises adding at least one substance capable of up-regulating IL-12R on the T-lymphocytes.

10. A method according to claim 1, wherein the second phase comprises adding one or more substances capable of antagonizing development of Th2 type T-lymphocytes.

11. A method according to claim 10, wherein the one or more substances capable of antagonizing development of Th2 type T-lymphocytes are one or more substances capable of neutralizing IL-4, IL-5, IL-10, and/or TGF-beta.

12. A method according to claim 11, wherein the one or more substances capable of neutralizing IL-4, IL-5, IL-10, and/or TGF-beta are anti IL-4 antibody, anti IL-5 antibody and/or anti IL-10 antibody.

13. A method according to any of claims 1, 11 or 12, wherein a further amount of the one or more substance capable of antagonizing development of Th2 type T-lymphocytes is added regularly throughout the second phase.

14. A method according to claim 1, wherein the second phase comprises adding one or more substances promoting the development of Th1 type T-lymphocytes.

15. A method according to claim 14, wherein the one or more substances promoting the development of Th1 type T-lymphocytes is a substance having agonistic activity towards the IL-7, IL-12, IL-15 or IL-21 receptor.

16. A method according to claim 15, wherein the one or more substances is selected from IL-7, IL-12, IL-15 and IL-21.

17. A method according to any of claims 11, 14 or 15 for the preparation of Th1 type T-lymphocytes of the memory or effector type.

18. A method according to claim 1, further comprising monitoring the expression of cell surface markers, on the T-lymphocytes continuously during the first phase and second phase and wherein the T-lymphocytes are harvested when CD25 on T-lymphocytes in the second phase is down-regulated.

19. A method according to claim 18, wherein the T-lymphocytes are subjected to at least one additional round of the second phase when CD25 on T-lymphocytes is down-regulated.

20. A method according to claim 1, wherein the T-lymphocytes are derived from lymph nodes draining the malignant melanoma tumour and/or a metastasis thereof, or they are derived from blood.

21. A method according to claim 1, wherein the tumour-derived antigen is autologous tumour-derived antigen.

22. A method according to claim 1, wherein the tumour-derived antigen is autologous denatured tumour extract.

23. A method for treating a patient suffering from malignant melanoma, the method comprising administering tumour-reactive T-lymphocytes to the patient, wherein the T-lymphocytes are CD4+ helper or CD8+ T-lymphocytes and are obtained by:
  i) identifying in a patient one or more sentinel or metinel lymph nodes draining a malignant melanoma tumour or a metastasis from a malignant melanoma tumour;
  ii) resecting the one or more lymph nodes and, optionally all or part of the tumour or metastasis;
  iii) isolating tumour-reactive T-lymphocytes from said lymph nodes; and
  iv) in vitro expanding said tumour-reactive T-lymphocytes, wherein the in vitro expansion comprises
  a) a first phase of stimulating tumour-reactive CD4+ helper or CD8+ T-lymphocytes with tumour-derived antigen together with at least one substance having agonistic activity towards the IL-2 receptor to promote survival of tumour-reactive CD4+ helper or CD8+ T-lymphocytes, and
  b) a second phase of activating and promoting growth of tumour-reactive CD4+ helper or CD8+ T-lymphocytes, wherein the second phase is initiated when a CD25 cell surface marker or IL-2R marker is down-regulated on T-lymphocytes.

* * * * *